(12) United States Patent
Eddington et al.

(10) Patent No.: US 8,501,462 B2
(45) Date of Patent: Aug. 6, 2013

(54) INSERT DEVICE FOR MULTIWELL PLATE

(75) Inventors: David Eddington, Wheaton, IL (US);
Ki-Hwan Nam, Seattle, WA (US);
Shawn C. Oppegard, Fox River Grove, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 475 days.

(21) Appl. No.: 12/527,897

(22) PCT Filed: Feb. 27, 2008

(86) PCT No.: PCT/US2008/055134
§ 371 (c)(1),
(2), (4) Date: Oct. 9, 2009

(87) PCT Pub. No.: WO2008/106515
PCT Pub. Date: Sep. 4, 2008

(65) Prior Publication Data
US 2010/0112690 A1 May 6, 2010

Related U.S. Application Data

(60) Provisional application No. 60/904,114, filed on Feb. 27, 2007, provisional application No. 60/956,613, filed on Aug. 17, 2007, provisional application No. 61/023,338, filed on Jan. 24, 2008.

(51) Int. Cl.
*C12M 1/12* (2006.01)
*C12M 1/00* (2006.01)

(52) U.S. Cl.
CPC ............... *C12M 29/04* (2013.01); *C12M 29/10* (2013.01); *C12M 23/34* (2013.01)
USPC ........................................ 435/297.2; 435/374

(58) Field of Classification Search
CPC ...... C12M 29/04; C12M 29/10; C12M 29/16; C12M 23/24; C12M 23/34
USPC ............................... 435/297.5, 374; 156/245
See application file for complete search history.

(56) References Cited

U.S. PATENT DOCUMENTS 5,863,792 A 1/1999 Tyndorf et al.
6,475,774 B1 11/2002 Gupta
(Continued)

FOREIGN PATENT DOCUMENTS
EP 1739164 1/2007

OTHER PUBLICATIONS

Abraham et al., High content screening applied to large-scale cell biology, *Trends Biotechnol.*, 22:15-22 (2004).
(Continued)

*Primary Examiner* — Michael Hobbs
(74) *Attorney, Agent, or Firm* — Marshall, Gerstein & Borun LLP

(57) ABSTRACT

An assembly comprises a multiwell test plate having a plurality of wells having an opening and a base surface, an insert plate having a plurality of inserts positioned to align with a corresponding one of the wells whereby the insert plate can be nested with the multiwell plate. Each of the inserts includes a supply port arranged for flow communication with a supply source, an exhaust port, a bottom portion having a plurality of channels extending between the supply port and the exhaust port, and a gas permeable membrane covering the bottom portion. Each of the inserts is sized to position the gas permeable membrane a desired distance from the base surface of the multiwell test plate when the multiwell test plate and the insert plate are coupled to one another.

13 Claims, 16 Drawing Sheets

(56) References Cited

U.S. PATENT DOCUMENTS

| | | | |
|---|---|---|---|
| 6,908,767 B2 | 6/2005 | Bader | |
| 6,939,709 B2 | 9/2005 | Henderson et al. | |
| 7,118,909 B2 | 10/2006 | Gevaert et al. | |
| 7,169,602 B2 | 1/2007 | Sandell | |
| 2003/0215941 A1* | 11/2003 | Campbell et al. | 435/325 |
| 2004/0087005 A1* | 5/2004 | Henderson et al. | 435/283.1 |
| 2005/0176155 A1 | 8/2005 | Klein et al. | |
| 2007/0015179 A1 | 1/2007 | Klapperich et al. | |
| 2007/0037278 A1 | 2/2007 | Rodgers et al. | |

OTHER PUBLICATIONS

Allen et al., Formation of steady-state oxygen gradients in vitro: application to liver zonation, *Biotechnol. Bioeng.*, 82:253-62 (2003).

Allen et al., Oxygen modulation of cytochrome P540 pathways: role of oxygen gradients and HIF-1alpha in hepatocytes in vitro, *Hepatology AASLD Abstracts*, 38:270a (2003).

Alvarez et al., Reactive oxygen intermediates mediate a systemic signal network in the establishment of plant immunity, *Cell*, 92:773-84 (1998).

Anderson et al., Crystal structure of a hyperactive *Escherichia coli* glycerol kinase mutant Gly230→ Asp obtained using microfluidic crystallization devices, *Biochemistry*, 46:5722-31 (2007).

Beebe et al., Functional hydrogel structures for autonomous flow control inside microfluidic channels, *Nature*, 404:588-90 (2000).

Bhatia et al., Controlling cell interactions by micropatterning in co-cultures: hepatocytes and 3T3 fibroblasts, *J. Biomed. Mater. Res.*, 34:189-99 (1997).

Bhatia et al., Effect of cell-cell interactions in preservation of cellular phenotype: cocultivation of hepatocytes and nonparenchymal cells, *FASEB J.*, 13:1883-900 (1999).

Borkholder et al., Microelectrode arrays for stimulation of neural slice preparations, *J. Neurosci. Methods*, 77:61-6 (1997).

Carraway et al., Photophysics and photochemistry of oxygen sensors based on luminescent transition-metal complexes, *Anal. Chem.*, 63:337-42 (1991).

Chen et al., Geometric control of cell life and death, *Science*, 276:1425-8 (1997).

Chiu et al., Patterned deposition of cells and proteins onto surfaces by using three-dimensional microfluidic systems, *Proc. Natl. Acad. Sci. USA*, 97:2408-13 (2000).

Drew et al., Oxygen deficiency and root metabolism: Injury and acclimation under hypoxia and anoxia, *Annu. Rev. Plant Physiol. Plant Mol. Biol.*, 48:223-50 (1997).

Duffy et al., Rapid prototyping of microfluidic systems in poly(dimethylsiloxane), *Anal. Chem.*, 70:4974-84 (1998).

Eddington et al., A valved responsive hydrogel microdispensing device with integrated pressure source, *J. Microelectromechanical Systems*, 13:586-93 (2004).

Flaim et al., An extracellular matrix microarray for probing cellular differentiation, *Nat. Methods*, 2:119-25 (2005).

Folch et al., Microfabricated elastomeric stencils for micropatterning cell cultures, *J. Biomed. Mater. Res.*, 52:346-53 (2000.

Galbraith et al., Forces on adhesive contacts affect cell function, *Curr. Opin. Cell Biol.*, 10:566-71 (1998).

Giuliani et al., Central necrosis in isolated hypoxic human pancreatic islets: evidence for postisolation ischemia, *Cell Transplant*, 14:67-76 (2005).

Gross et al., Stimulation of monolayer networks in culture through thin-film indium-tin oxide recording electrodes, *J. Neurosci. Methods*, 50:131-43 (1993).

Haddad, Oxygen-sensitive pro-inflammatory cytokines, apoptosis signaling and redox-responsive transcription factors in development and pathophysiology, *Cytokines Cell Mol. Ther.*, 7:1-14 (2002).

Harvey, The role of oxygen in ruminant preimplantation embryo development and metabolism, *Anim. Reprod. Sci.*, 98:113-28 (2007).

Heo et al., Characterization and resolution of evaporation-mediated osmolality shifts that constrain microfluidic cell culture in poly(dimethylsiloxane) devices, *Anal. Chem.*, 79:1126-34 11 (2007).

Holzer et al., Maintenance of periportal and pericentral oxygen tensions in primary rat hepatocyte cultures: influence on cellular DNA and protein content monitored by flow cytometry, *J. Cell Physiol.*, 133:307-304 (1987).

International Preliminary Report on Patentability for corresponding International Application No. PCT/US08/55134, dated Sep. 1, 2009.

International Search Report and Written Opinion of corresponding International Application No. PCT/US08/55134, dated Jul. 24, 2008.

Khademhosseini et al., Microscale technologies for tissue engineering and biology, *Proc. Natl. Acad. Sci. USA*, 103:2480-7 2006.

Kondo et al., Inhibition of HIF is necessary for tumor suppression by the von Hippel-Lindau protein, *Cancer Cell*, 1:237-46 (2002).

Kong et al., Parallel gene synthesis in a microfluidic device, *Nucleic Acids Res.*, 35:e61 (2007).

Lee et al., Microbioreactor arrays with integrated mixers and fluid injectors for high-throughput experimentation with pH and dissolved oxygen control, *Lab Chip*, 6:1229-35 (2006).

Lee et al.. Multistep synthesis of a radiolabeled imaging probe using integrated microfluidics, *Science*, 310:1793-6 (2005).

LI et al., Extracellular heat shock protein-90alpha: linking hypoxia to skin cell motility and wound healing, *EMBO J.*, 26:1221-33 (2007).

Li et al., Nanoliter microfluidic hybrid method for simultaneous screening and optimization validated with crystallization of membrane proteins, *Proc. Natl. Acad. Sci. USA*, 103:19243-8 (2006).

Lin et al., Assessing porcine liver-derived biomatrix for hepatic tissue engineering, *Tissue Eng.*, 10:1046-53 (2004).

Lin et al., Inhibition and induction of cytochrome P450 and the clinical implications, *Clin. Pharmacokinet.*, 35:361-90 (1998).

Lucchetta et al., Dynamics of *Drosophila* embryonic patterning network perturbed in space and time using microfluidics, *Nature*, 434:1134-8 (2005).

Marcus et al., Parallel picoliter rt-PCR assays using microfluidics, *Anal. Chem.*, 78:956-8 (2006).

Masur et al., Myofibroblasts differentiate from fibroblasts when plated at low density, *Proc. Natl. Acad. Sci. USA*, 93:4219-23 (1996).

Maxwell et al., Oxygen sensors and angiogenesis, *Semin. Cell Dev. Biol.*, 13:29-37 (2002).

Mehta et al., Quantitative measurement and control of oxygen levels in microfluidic poly(dimethylsiloxane) bioreactors during cell culture, *Biomed. Microdevices*, 9:123-34 (2007).

Mukhopadhyay, When PDMS isn't the best. What are its weaknesses, and which other polymers can researchers add to their toolboxes?, *Anal. Chem.*, 79:3248-53 (2007).

Narasimhan et al., Polymer embossing tools for rapid prototyping of plastic microfluidic devices, *J. Micromechanics Microengineering*, 14:96-103 (2004).

Ottesen et al.. Microfluidic digital PCR enables multigene analysis of individual environmental bacteria, *Science*, 314:1464-7 (2006).

Pardo et al., Characterization of patterned self-assembled monolayers and protein arrays generated by the ink-jet method, *Langmuir*, 19:1462-6 (2003).

Parmar et al., Distribution of hematopoietic stem cells in the bone marrow according to regional hypoxia, *Proc. Natl. Acad. Sci. USA*, 104:5431-6 (2007).

Paul et al., Lamination-based rapid prototyping of microfluidic devices using flexible thermoplastic substrates, *Electrophoresis*, 28:1115-22 (2007).

Randall et al., Permeation-driven flow in poly(dimethylsiloxane) microfluidic devices, *Proc. Natl. Acad. Sci. USA*, 102:10813-8 (2005).

Reyes et al., Micro total analysis systems. 1. Introduction, theory, and technology, *Anal. Chem.*, 74:2623-36 (2002).

Risbud et al., Nucleus pulposus cells express HIF-1 alpha under normoxic culture conditions: a metabolic adaptation to the intervertebral disc microenvironment, *J. Cell Biochem.*, 98:152-9 (2006).

Roman et al., Sol-gel modified poly(dimethylsiloxane) microfluidic devices with high electroosmotic mobilities and hydrophilic channel wall characteristics, *Anal. Chem.*, 77:1414-22 (2005).

Rosen et al., Effect of varying oxygen concentrations on the proliferation of retinal microvascular cells in vitro, *Exp. Eye Res.*, 53:597-601 (1991).

Schwartz et al., Networks and crosstalk: integrin signalling spreads, *Nat. Cell Biol.*, 4:E65-8 (2002).

Singhvi et al., Engineering cell shape and function, *Science*, 264:696-8 (1994).

Squires et al., Microfluidics: fluid physics at the nanoliter scale, *Rev. Modern Physics*, 77:977-1026 (2005).

Tan et al., Cells lying on a bed of microneedles: an approach to isolate mechanical force, *Proc. Natl. Acad. Sci. USA*, 100:1484-9 (2003).

Tilles et al., Effects of oxygenation and flow on the viability and function of rat hepatocytes cocultured in a microchannel flat-plate bioreactor, *Biotechnol. Bioeng.*, 73:379-89 (2001).

Uno et al., Hyperoxia inhibits several critical aspects of vascular development, *Dev. Dyn.*, 236:981-90 (2007).

Vollmer et al., Development of an integrated microfluidic platform for dynamic oxygen sensing and delivery in a flowing medium, *Lab Chip*, 5:1059-66 (2005).

Wang et al., Hypoxia-inducible factor 1 is a basic-helix-loop-helix-PAS heterodimer regulated by cellular O2 tension, *Proc. Natl. Acad. Sci. USA*, 92:5510-4 (1995).

Ye et al., DNA separation with low-viscosity sieving matrix on microfabricated polycarbonate microfluidic chips, *Anal. Bioanal. Chem.*, 381:820-7 (2005).

\* cited by examiner

1. Coat a Si Wafer with Photoresist

2. Expose to UV Light through a Photomask to Polymerize Photoresist

3. Wash Away Unexposed Photoresist

4. Cure PDMS on Mold

5. Release PDMS, Bond to Pillar

FIG. 14A
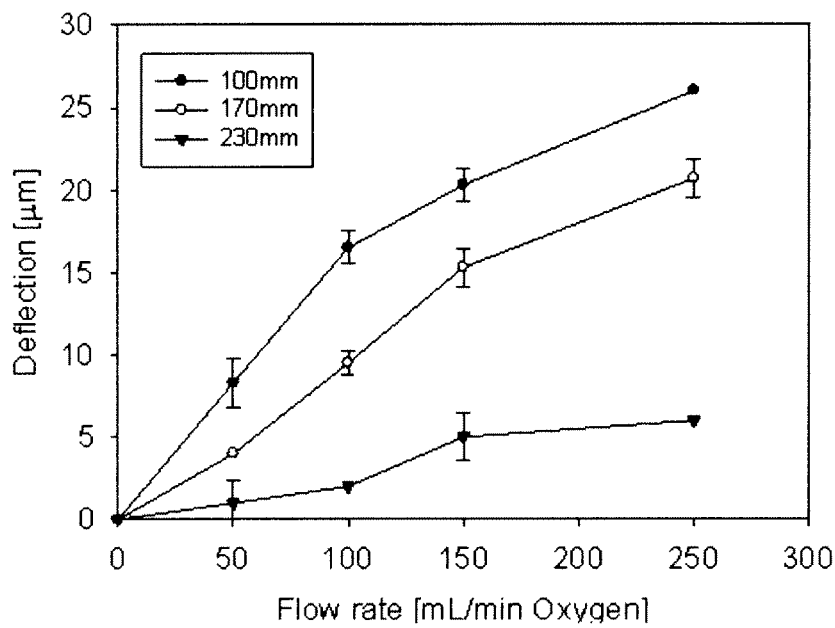
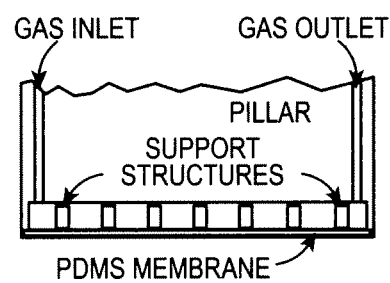
FIG. 14B
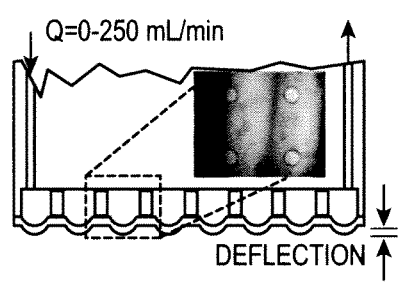
FIG. 14C

INSERT DEVICE FOR MULTIWELL PLATE

CROSS-REFERENCE TO RELATED APPLICATIONS

This application claims the benefit under 35 U.S.C. §119 of U.S. provisional application Nos. 60/904,114, filed Feb. 27, 2007; 60/956,613, filed Aug. 17, 2007; and 61/023,338, filed Jan. 24, 2008, each of which is incorporated by reference in its entirety herein.

BACKGROUND

In order to gain widespread acceptance, new technology in biomedical research fields typically should address current unmet experimental needs, and should be relatively easy to integrate into standard research lab protocol. Many advances require researchers to discard well accepted protocols and in favor of more complex devices, methods, or materials. For example, the hesitancy of researchers to adopt unfamiliar and potentially more complex protocols has stymied broad dissemination of Bio-MicroElectroMechanical Systems (bioMEMS). Researchers also are hesitant to use and fabricate complex bioMEMS devices in highly variable biological systems when the possible gains seem marginal at best. In order for the field of bioMEMS to mature beyond proof-of-concept demonstrations, researchers may soon focus on developing systems using microscale phenomena, and may work to integrate these phenomena into standard laboratory methods.

The primary methods for oxygen variation in standard cell biology experimental protocols typically involve either changing the global incubator oxygen concentration or using modular hypoxic chambers. Modular hypoxic chambers offer a simple approach to compartmentalize standard incubators into several oxygen concentrations. However, the size of these chambers limits the number of hypoxic chambers (and consequently conditions) to three to four for each incubator, and reduces the remaining available incubator space for other investigations. Because incubators are large and expensive, limiting the available incubator space to accommodate only ten multiwell plates is far from ideal. These issues are especially important when working with highly variable primary mammalian cells because performing all experiments on the same batch of cells reduces inherent animal to animal variability.

Realizing these limitations, several groups have developed devices to control the oxygen environment around adherent cell cultures (Tilles, et al. *Biotechnology and Bioengineering* 73(5): 379-389 (2001); Allen et al., *Biotechnology and Bioengineering* 82(3): 253-262 (2003); Vollmer, et al., *Lab on a Chip* 5(10): 1059-1066 (2005); Lee, et al. *Lab on a Chip* 6(9): 1229-1235 (2006); Mehta, et al., *Biomedical Microdevices* 9(2): 123-134 (2007)). However, these devices are specialized for their unique application and require complex fluidic handling and controls to maintain the cells under perfusion, which impedes widespread adoption of these techniques. Other demonstrations of oxygen control in microfluidic channels used electrolysis to generate oxygen (Vollmer, et al., *Lab on a Chip* 5(10): 1059-1066 (2005)), which further complicates device fabrication and operation. Thus, a need exists for improved devices and methods for controlling gas (e.g., oxygen) concentrations within a multiwell plate.

SUMMARY OF THE INVENTION

In accordance with a disclosed example, an assembly comprises a multiwell plate having a plurality of wells, with each of the wells having an opening and a base surface, and an insert plate having a plurality of inserts positioned to align with a corresponding one of the wells whereby the insert plate can be coupled to the multiwell test plate with each insert disposed in the corresponding well. Each of the inserts may include a supply port arranged for flow communication with a supply source, an exhaust port, a bottom portion, a gas permeable membrane secured to the bottom portion, and a flow channel formed between the gas permeable membrane and the bottom portion of the insert, the flow channel providing flow communication between the supply port and the exhaust port. Each of the inserts may have a length sized to position the gas permeable membrane a desired distance from the base surface of the multiwell plate when the multiwell plate and the insert plate are coupled to one another.

In further accordance with one or more preferred examples, the bottom portion of each of the inserts may parallel to the base surface of the corresponding well, and the multiwell plate may have a support surface such that a portion of the insert plate rests on the upper surface. The length of each of the inserts is sized based on a distance from the support surface to the base surface.

Each of the inserts may have a first side and a second side, and the channel extends from adjacent the first side to adjacent the second side. Each of the inserts and each of the wells may have a circular cross-section, and each of the inserts may have a plurality of sidewalls with each of the wells having a plurality of sidewalls, such that each insert sidewall is parallel to a corresponding well sidewall. The gas permeable membrane preferably includes a plurality of upwardly extending protrusions, with the flow channel extending between adjacent protrusions. An upper portion of the protrusions may be secured to the bottom portion of the insert, and the protrusions are sized to maintain the gas permeable membrane a selected distance from a surface of the bottom portion of the insert.

Preferably, the membrane is constructed of polydimethylsiloxane (PDMS), and the desired distance may be about 100 µm to about 200 µm. The base surface of each of the wells also may be curved and the bottom surface of each of the inserts may be generally planar, such that the desired distance includes a first distance measured from adjacent a sidewall of the insert to the base surface and a second distance measured from adjacent a center of the insert to the base surface, and wherein the first and second distances are between about 100 µm to about 200 µm.

The gas permeable membrane preferably covers a first portion of the insert, and wherein at least one of the inserts may include a second supply port connectable to a second supply source, a second exhaust port, and a second plurality of channels extending between the second supply port and the second exhaust port, with a second gas permeable membrane covering a second portion of the bottom surface and overlying the second plurality of channels. The gas permeable membrane also may have a thickness of about 50 µm to about 200 µm. The supply port of each insert may be in flow communication with a supply manifold, the exhaust port of each insert may be in flow communication with an exhaust manifold.

In accordance with another disclosed example, a device for introducing a gas to a multiwell plate having a plurality of wells may comprise an insert plate, the insert plate arranged to be coupled to the multiwell plate and having a plurality of inserts positioned to align with a corresponding one of the wells of the multiwell plate, whereby the each of the inserts can be positioned in a corresponding one of the wells of the multiwell plate when the insert plate is coupled to the multiwell plate. Each of the inserts may include a supply port connectable to a supply source, an exhaust port, a bottom portion, a gas permeable membrane secured to the bottom portion, and a flow channel formed between the gas permeable membrane and the bottom portion and extending between the supply port and the exhaust port. Each of the inserts has a length sized to position the gas permeable membrane a desired distance from the base surface of the multiwell plate when the multiwell plate and the insert plate are coupled to one another.

In accordance with a further disclosed example, a method of preparing a gas permeable insert device for use with a multiwell plate comprises coating a silicon wafer with a photoresist material, applying a material impervious to UV light onto the coated silicon wafer to mask at least a portion of the surface of the coated silicon water, exposing the masked coated silicon wafer to UV light to etch the unmasked portions of the coated silicon wafer to form a mold, depositing a prepolymer mixture of a gas permeable material on the mold under conditions suitable to form of a membrane of a selected thickness and having a channel structure, and adhering the membrane to a bottom portion of a column provided with a supply port and an exhaust port such that the channel structure permits flow communication between the supply port and the exhaust port.

In accordance with yet another disclosed example, a method of controlling a gas concentration in a well of a multiwell plate comprises providing a channel structure on a bottom portion of an insert column, providing an inlet port and an exhaust port, covering the channel structure with a gas permeable membrane to form a flow path between the inlet port and the outlet port through the channel structure, positioning the insert column in a well with the membrane a desired distance from a base surface of the well, and connecting a first gas supply source to the inlet port and delivering a first gas having a first concentration though the channel structure such that the well is exposed to the first gas.

BRIEF DESCRIPTION OF THE DRAWINGS

FIG. 14 shows measured deflection of membranes of various thicknesses at various flow rates;

DETAILED DESCRIPTION

Although the following text sets forth a detailed description of exemplary embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, with those alternative embodiments still falling within the scope of the claims defining the invention.

Figure 1:
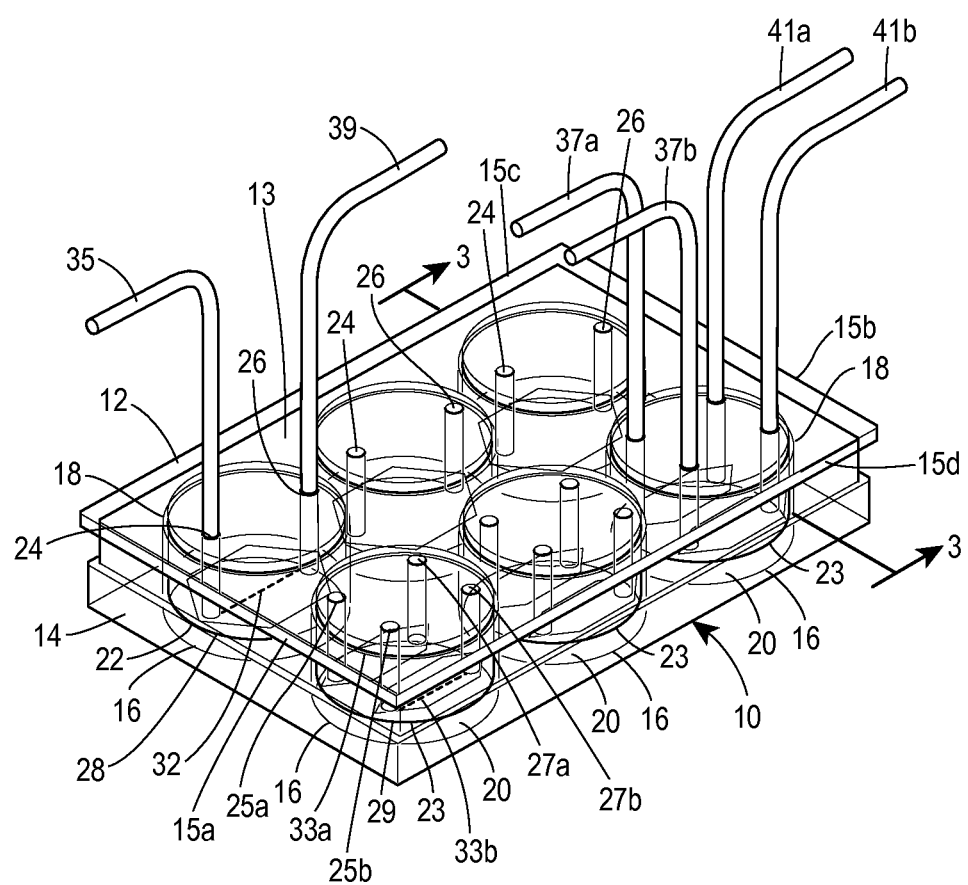
FIG. 1 is a perspective view of an assembly including an insert plate shown nested with a multiwell plate and assembled in accordance with the teachings of a disclosed example of the present invention.
Figure 2:
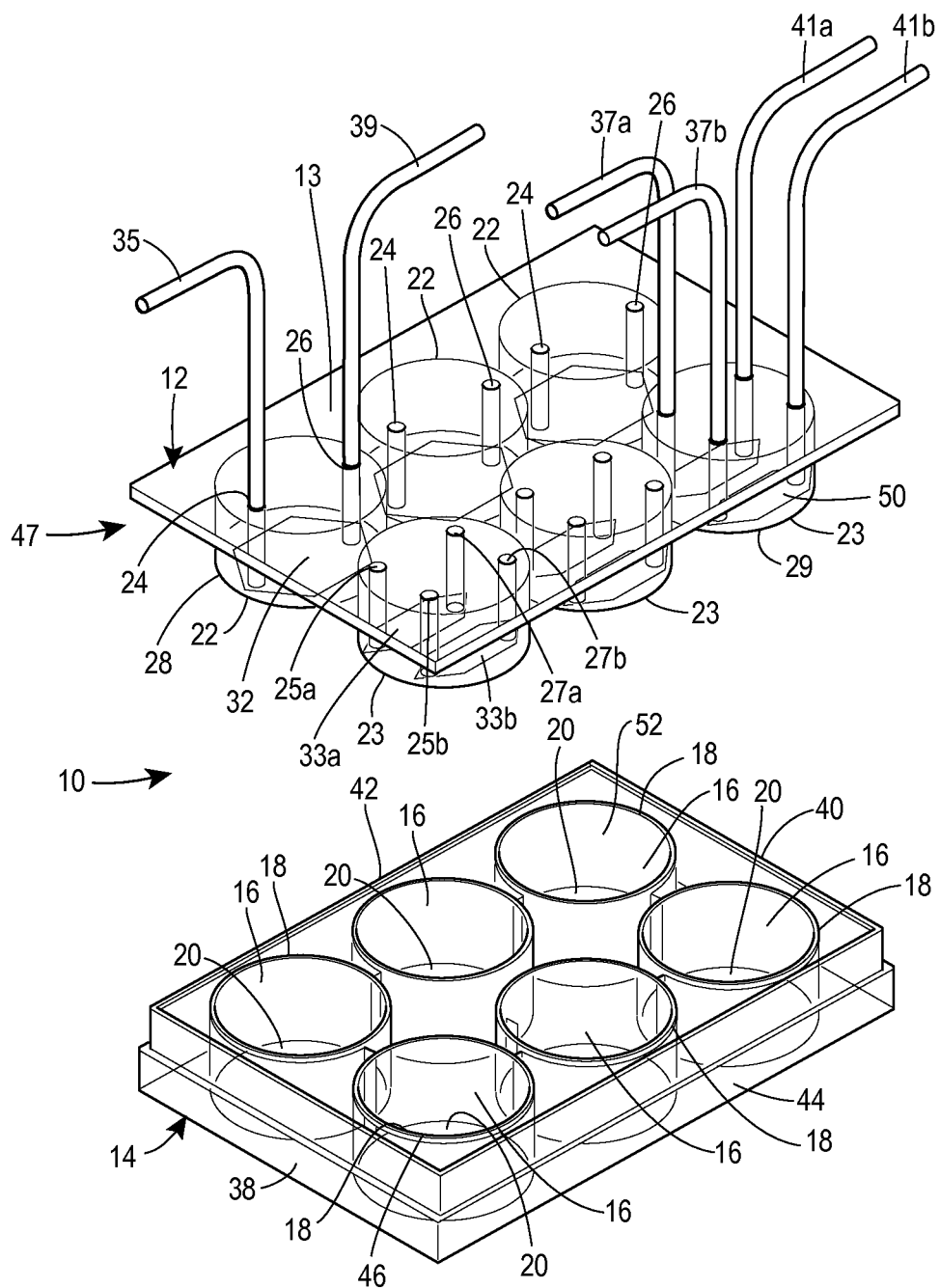
FIG. 2 is an exploded view of the assembly of FIG. 1 and illustrating the insert plate spaced away from the multiwell plate.

Referring now to FIGS. 1 and 2, an assembly constructed in accordance with the teachings of an example of the present invention is shown and is identified generally by the reference numeral 10. The assembly 10 includes an insert plate 12 and a multiwell plate 14. The multiwell plate includes a plurality of individual wells 16, with each of the wells 16 having an opening 18 and a base surface 20. The insert plate 12 includes a generally planar top portion 13, and includes a plurality of individual inserts 22 and a plurality of individual inserts 23. Each of the inserts 22, 23 is positioned to align with a corresponding one of the wells 16 of the multiwell plate 14, such that the insert plate 12 can be coupled to or otherwise suitably attached to the multiwell plate 14 with each individual insert 22, 23 disposed in the corresponding well 16 in a nested fashion. In the example of FIGS. 1 and 2, the inserts 22 differ from the inserts 23 in a manner to be explained in greater detail below. Alternatively, all of the inserts of the insert plate 12 may be identical. FIGS. 3-6 illustrate the exemplary inserts 22 and 23 greater detail. In the example of FIGS. 1 and 2, the insert plate 12 and the multiwell plate 14 are generally transparent or translucent.

The exemplary insert plate 12 is generally rectilinear in shape, and has a pair of ends 15a and 15b, and a pair of sidewalls 15c and 15d. Other shapes may prove suitable. Each insert 22 includes a supply port 24, an exhaust port 26, and a bottom portion 28. Similarly, each insert 23 includes a pair of supply ports 25a and 25b, a pair of exhaust ports 27a and 27b, and a bottom portion 29. The bottom portions 28 and 29 each are covered by a gas permeable membrane 30 (mostly ibscured in FIGS. 1 and 2, but visible in FIGS. 3-6). A flow channel 32 is formed between the gas permeable membrane 30 and the bottom portion 28 of the pillar or column that forms the insert 22, and a pair of flow channels 33a and 33b are formed between the gas permeable membrane 30 and the bottom portion 29 of the pillar or column that forms the insert 23. Accordingly, the flow channel 32 provides flow communication between the supply port 24 and the exhaust port 26 of the insert 22, the flow channel 33a provides flow communication between the supply port 25a and the exhaust port 27a, and the flow channel 33b provides flow communication between the supply port 25b and the exhaust port 27b. The inserts 22 and 23 each have a length L sized to position a bottom surface 31 of the gas permeable membrane 30a desired distance D from the base surface 20 of the multiwell plate 14 when the multiwell plate 14 and the insert plate 12 are coupled to one another. In accordance with a preferred example, the membrane 30 is preferably constructed of polydimethylsiloxane (PDMS). Other materials may prove suitable. The entire insert plate 12 also may be constructed of PDMS. In further accordance with the disclosed example, the length L of the inserts 22 and 23 are the same. Alternatively, the inserts 22 and 23 may have different lengths. Consequently, the desired distance D for the insert 22 may be the same or different compared to the desired distance D for the insert 23.

A supply conduit 35 is connected to the supply port 24 for each of the inserts 22, while a supply conduit 37a is connected to the supply port 25a and a supply conduit 37b is connected to the supply port 27b for each of the inserts 23. The supply conduits 35, 37a and 37b are connectable to a gas source (not shown, but discussed in greater detail below). An exhaust conduit 39 is connected to the exhaust port 26 for each of the inserts 22, while an exhaust conduit 41a is connected to the exhaust port 27a and an exhaust conduit 41b is connected to the exhaust port 27b for each of the inserts 23. The exhaust conduits 39, 41a and 41b are connectable to an exhaust. Each of the conduits 35, 37a, 37b, 39, 41a and 41b may be flexible tubing.

Referring to FIG. 2, the multiwell plate 14 may be molded unitarily from a plastic material such as polyvinylchloride, polystyrene or polypropylene. Other materials may prove suitable. Alternatively, the multiwell plate 14 may be assembled from a plurality of component parts. In the form shown in FIGS. 1 and 2, the multiwell plate 14 has a substantially rectangular base 34 and a peripheral skirt 36 extending upwardly from base 34. The multiwell plate 14 may be generally rectilinear having first and second substantially parallel end walls 38 and 40 and first and second substantially parallel sidewalls 42 and 44. The multiwell plate 14 generally defines a rectangular array 46 of the individual wells 16, which matches an array 47 of the inserts 22,23. The wells shown are generally cylindrical and have a circular horizontal cross-section, although the cross-section of the wells 22 also may be rectilinear or any other suitable shape. The dimensions of the wells 22, as well as the dimensions of the multiwell plate 14, preferably conform to industrial standards to ensure compatibility with available laboratory equipment. In the illustrated embodiment, the array 46 includes 6 wells, although the array 46 may include any desired number of individual wells, or may include a number corresponding to the number typically available in commercially available multiwell plates. As shown, the base surface 20 of the wells 16 are flat. Alternatively, the base surface may be curved or rounded.

Figure 4:
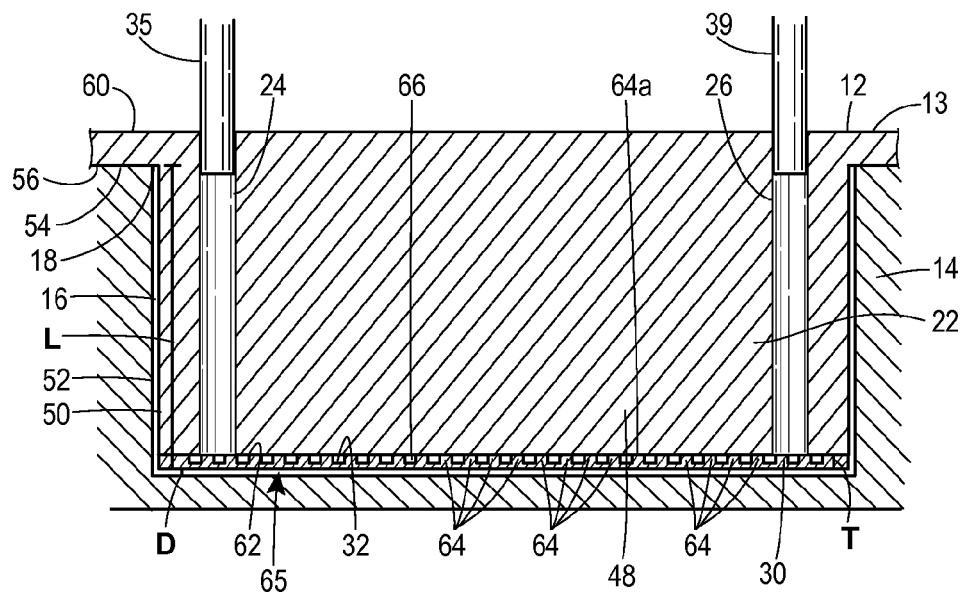
FIG. 4 is an enlarged fragmentary cross-sectional view taken along line 4-4 of FIG. 3 and showing an exemplary flow channel extending across a lower portion of the insert between the supply port and the exhaust port.

In accordance with a preferred embodiment, and as visible in FIG. 4, a thickness T of the membrane 30 may be about 100 μm, although a broader range of about 50 to about 200 μm may suffice. Other thicknesses may prove suitable. The thickness may be chosen to balance the benefit of rapid gas transport with the limitation of increased deflection under applied pressures with thinner membranes. For example, a membrane having a thickness less than 100 μm may tear when exposed to certain pressures, or may deform beyond acceptable or desired limits. A membrane having a thickness too great may inhibit gas permeation through the material, which may lead to uncertainty regarding the actual gas concentration exposure within the well.

In accordance with a preferred embodiment, an exemplary desired distance D between the membrane 30 and the base surface 20 of the well 16 may be in a range of about 100 μm to about 200 μm. Other distances may prove suitable. In the event the base surface 20 of the well is curved, the distance measured at the center of the insert and the center of the well is in the desired range, as is the distance measured at the edge of the insert adjacent the edge of the well. In accordance with the disclosed example, the relatively close spacing between the membrane and well fosters rapid diffusion to impose steady state gradients of the gas across the well within minutes. Preliminary results show a slight deflection of the PDMS membrane 30 of about 25 μm.

Figure 3:
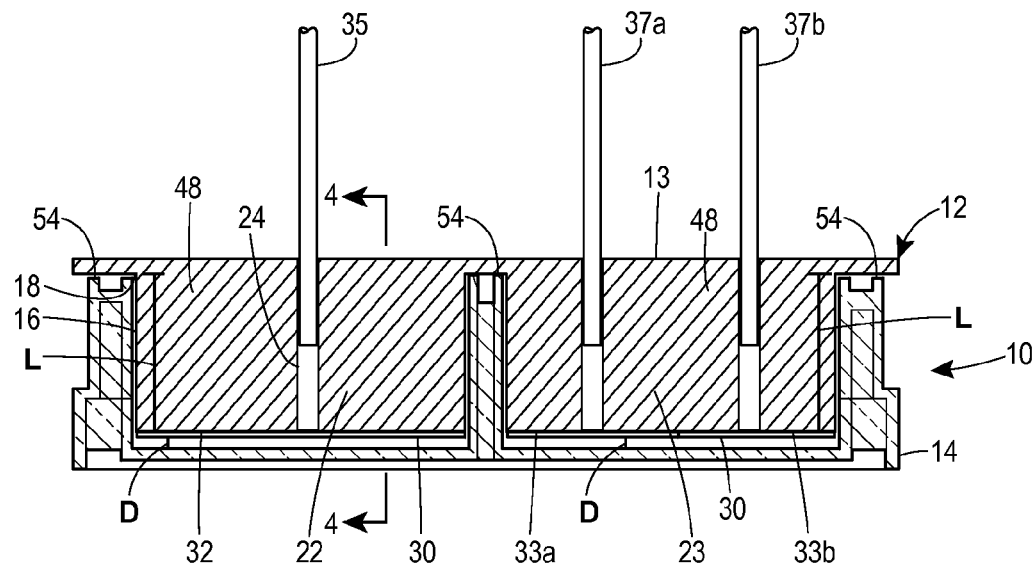
FIG. 3 is an enlarged fragmentary cross-sectional view taken along line 3-3 of FIG. 1 and showing an exemplary column structure forming an insert.

Referring now to FIG. 3, the inserts 22 and 23 are shown in an enlarged cross-section. The insert 22 is shown on the left disposed in its corresponding well 16, while the insert 23 is shown on the right disposed in its corresponding well 16. In the examples shown, the bottom portion 28 of the insert 22 is parallel to the base surface 20 of its corresponding well 16, and the bottom portion 29 of the insert 23 is parallel to the base surface 20 of its corresponding well 16. Each of the inserts 22 and 23 is generally in the shape of a pillar or generally cylindrical column 48 that depends downwardly from the top portion 13 of the insert plate 12. Each of the columns 48 have a surrounding sidewall 50 which, in the disclosed example, is parallel or generally parallel to a surrounding sidewall 52 of the corresponding well 16. Alternatively, the inserts 22 or 23 may have a generally rectangular or rectilinear horizontal cross-section having a plurality of sidewalls, and the cross-sectional shape of the corresponding wells 16 of the multiwell plate 14 may be shaped accordingly to also have a plurality of sidewalls.

As shown in FIGS. 3 and 4, a portion of the multiwell plate 14 defines one or more support surfaces 54. A lower surface 56 of the top portion 13 of the insert plate 12 rests on the support surface 54. Accordingly, the length L of the inserts 22, 23 is sized to maintain the membrane 30 the desired distance T from the base surface 20 of the corresponding well 16. The cross-section of FIG. 4, which is taken along the line 4-4 of FIG. 3, shows an exemplary cross-section of the insert 22. However, it will be understood that a similar cross-section taken through the insert 23 would be substantially similar to that shown in FIG. 4. For purposes of simplicity, only the cross-section through the insert 22 need be described in detail. The supply port 24 through the insert 22 is formed by an aperture or conduit 58 that extends through the column 48 from a top surface 60 of the insert plate 12 through a bottom surface 62 of the column 48. In accordance with the disclosed example, the membrane 30 includes a plurality of upwardly extending protrusions 64 which keep a portion of the membrane 30 spaced away from the bottom surface 62 of the corresponding column 48. In accordance with the disclosed example, the protrusions 64 are spaced apart from one another in an array or pattern 65, such as is shown in greater detail in FIG. 6. Consequently, the flow channel 32 between the supply port 24 and the exhaust port 26 is defined in part by a plurality of spaces 66 between adjacent protrusions 64. As will be explained in greater detail below, a top portion 64a of each of the protrusions 64 is preferably attached to the bottom surface 62 of the column 48.

Figure 5:
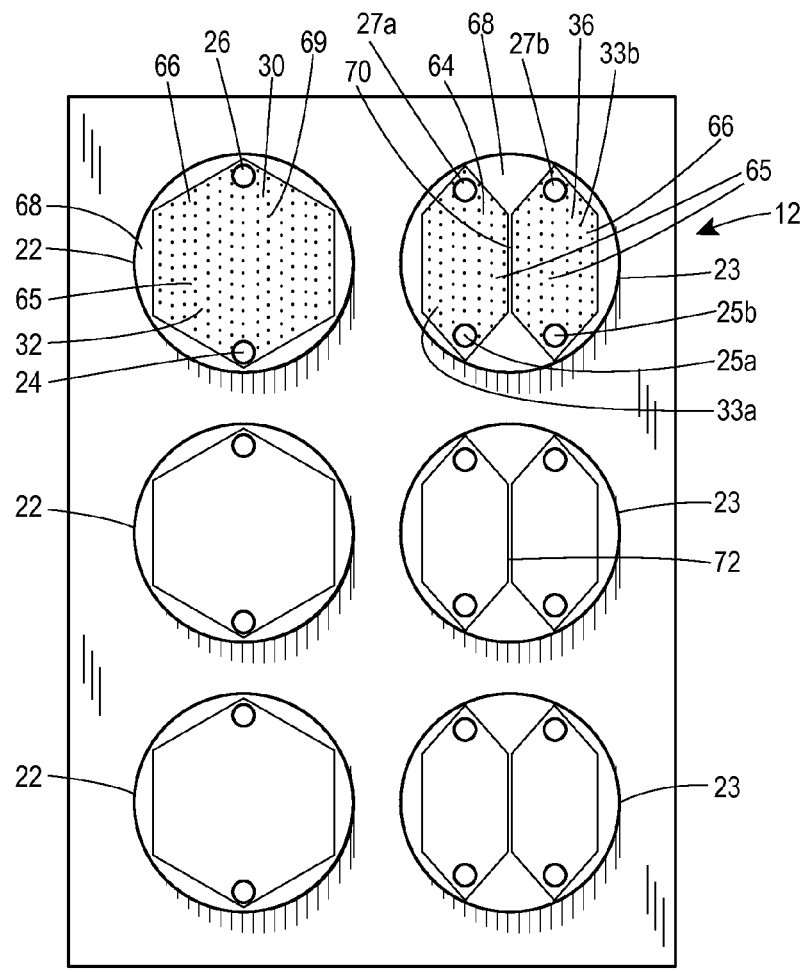
FIG. 5 is a bottom plan view of the insert plate and illustrating two exemplary configurations for the flow channels.
Figure 6:
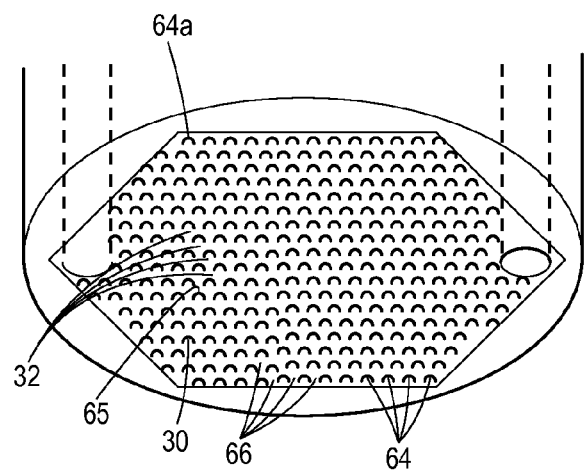
FIG. 6 is an enlarged perspective view of an exemplary gas permeable membrane having a pattern of protrusions.
Figure 16:
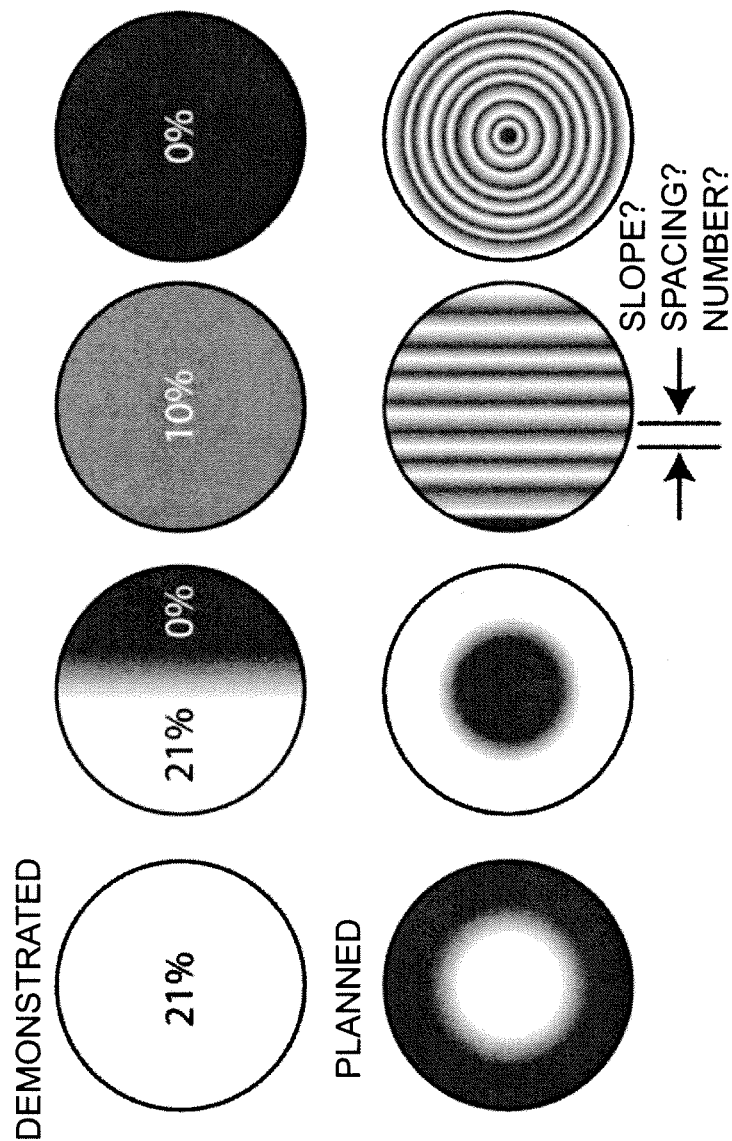
FIG. 16 shows a schematic of oxygen gradients to which a single well can be exposed using the devices as disclosed herein.

Referring now to FIG. 5, the bottom plan view shows an exemplary arrangement of the membranes 30 attached to the columns 48 to define the flow channels 32, 33a and 33b. For purposes of simplicity, the bottom plan view of FIG. 5 only shows the pattern 65 on one of the inserts 22 and one of the inserts 23. As shown in FIG. 5, the membrane 30 is preferably round and generally corresponds to the round shape of the bottom surface 62 of the columns 64. As shown in the upper left corner of FIG. 5, the flow channel 32 is generally formed by arranging the pattern 65 of the protrusions 64 in a generally hexagonal arrangement. An outer boundary 68 of the membrane 30 is secured to the bottom surface 62 of the corresponding column 48. Preferably, the upper portion 64a of each of the protrusions 64 and the outer boundary 68 are secured to the bottom surface 62 of the column 48 in the same manner. Still preferably, the upper portion 64a of each of the protrusions 64 and the outer boundary 68 are secured to the bottom surface 62 using oxygen plasma. Alternatively, other forms of attachment may prove suitable. As shown in the upper right corner of FIG. 5, the flow channels 33a and 33b are generally formed by arranging the pattern 65 of the protrusions 64 in a pair of generally hexagonal arrangements, with the flow channels 33a and 33b separated from one another by a boundary 70. The protrusions may be about 0.1 millimeters to about 5 millimeters in length, giving the flow channels a depth of about 0.1 millimeters to about 5 millimeters, although other lengths and other channel depths may prove suitable. An outer boundary 72 of the membrane 30 in the insert 23 is attached or otherwise secured to the bottom surface 62 in the same manner as the construction of the insert 22. Alternatively, the flow channels 32, 33a and 33b may take a variety of different forms other than those shown. For example, the flow channels may be defined by discrete or interconnected grooves formed on the bottom surface 62 of the columns 48. As another example, as shown in FIG. 16 two separate concentric flow channels may be formed, including an inner flow channel shown in dark gray, an outer flow channel shown in white, which are separated by a ring-shaped boundary shown in light gray. As is also shown in the lower right corner of FIG. 16, there may be an even greater number of concentric flow channels. Still other forms for individual or segregated flow channels may prove suitable.

Figure 7A:
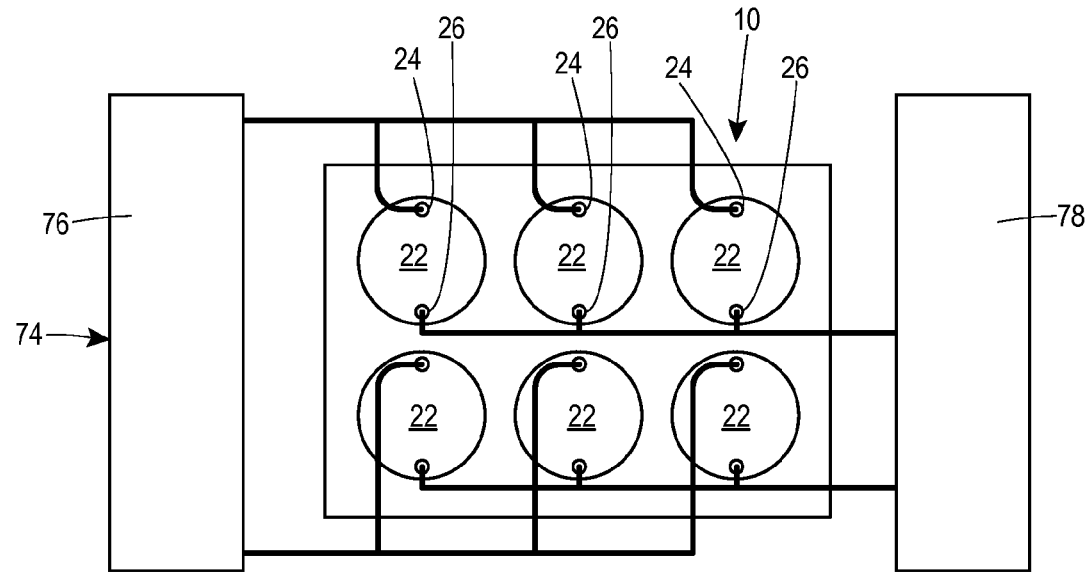
FIGS. 7A and 7B are top plan views in schematic of the insert plate of FIG. 1 and illustrating exemplary flow paths through the insert plate extending from a supply source, through an intake manifold, through the individual inserts, and out an exhaust manifold.

Referring now to FIG. 7A, an exemplary flow pattern through the assembly 10 is shown schematically. In the example of FIG. 7A, the assembly 10 includes six (6) inserts 22. It will be understood that the same teachings would apply to an assembly 10 having the inserts 23, or any combination of the inserts 22 and 23. The supply port 24 for each of the inserts 22 is connected to a gas supply source 74 via a common supply manifold 76. Similarly, the exhaust port for each of the inserts 22 is connected to a common exhaust manifold 78. In the example of FIG. 7A, each of the inserts 22 will be exposed to the same concentration of gas from the gas supply source due to the connection to the common supply manifold 76.

Figure 7B:
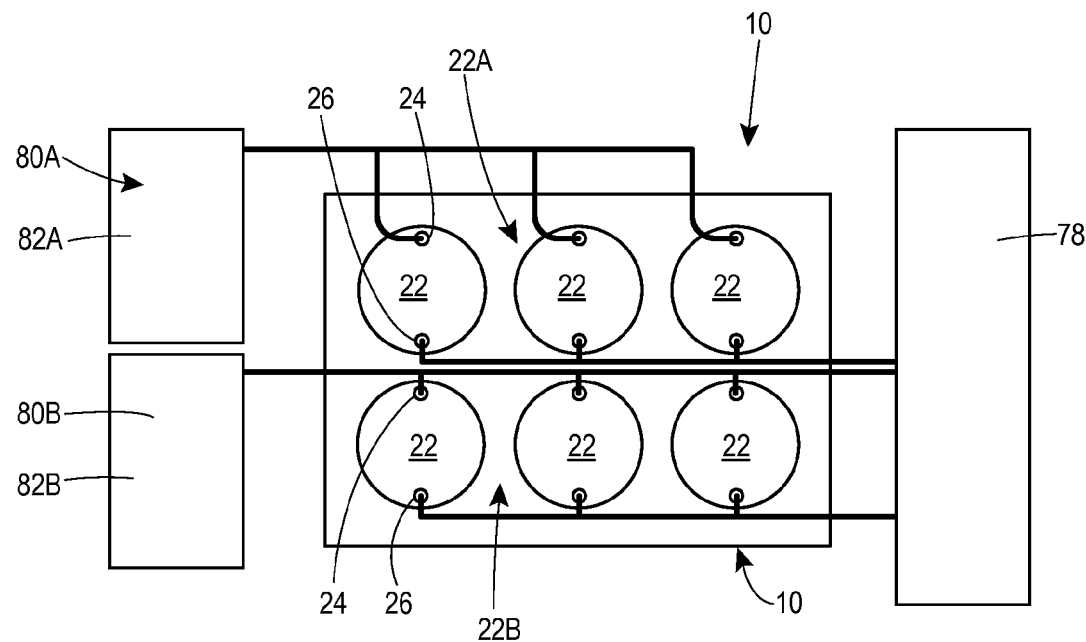

Referring now to FIG. 7B, another exemplary flow pattern through the assembly 10 is shown schematically. In the example of FIG. 7B, the supply port 24 for the first set 22A of the inserts 22 is connected to a first gas supply source 80A via a common supply manifold 82A, while another or second set 22B of the inserts 22 is connected to a second gas supply source 80B via a second common supply manifold 82B. All of the inserts 22 are connected to the common exhaust manifold 78. Alternatively, the inserts may be connected to segregated exhaust manifolds. Consequently, in the example of FIG. 7B, half of the inserts 22 will be exposed to gas at a first concentration, while the other half of the inserts will be exposed to gas a second concentration. As a further alternative, the inserts 22 may be divided into a number of different sets, with each of the different sets arranged to be connected to different supply manifolds in order to expose each of the sets to any gas at a selected concentration.

Figure 8:
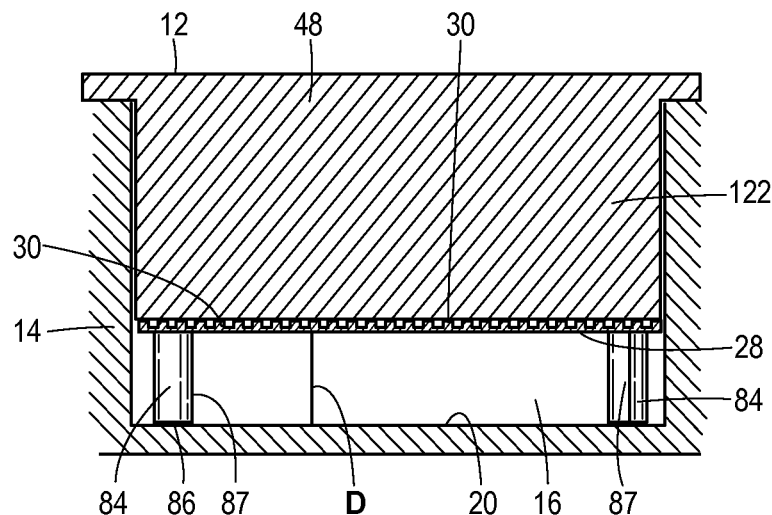
FIG. 8 is an enlarged fragmentary cross-sectional view similar to FIG. 3 and showing an alternative insert embodiment.

Referring now to FIG. 8, an alternative construction of the insert 122 is shown. The supply and exhaust ports have been omitted for clarity, and certain vertical dimensions have been exaggerated. The insert 122, which may be similar to either the insert 22 or the insert 23 described above, includes one or more supports or spacers 84 which extend downwardly from the column 48. A lower end 86 of each spacer 84 abuts the base surface 20 of the corresponding well 16. Each spacer 84 has a length 87 sized such that the spacer 84 maintains the membrane 30 at the desired distance D from the base surface 20 of the corresponding well 16. In all other respects, the insert 22 may be similar to the insert 22 described above. However, the column may be sized to be longer than the depth of the well 16.

Figure 9:
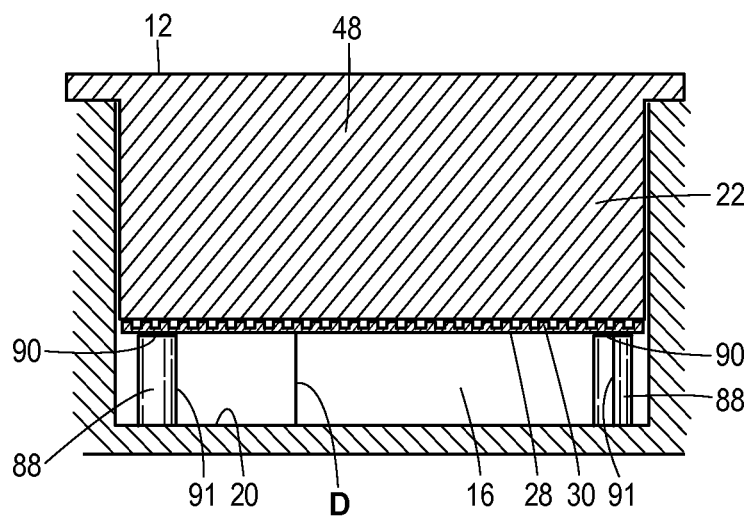
FIG. 9 is an enlarged fragmentary cross-sectional view similar to FIG. 3 and showing still another alternative embodiment in which the multiwell plate includes one or more support posts.

Referring now to FIG. 9, another alternative construction is shown. Again, supply and exhaust ports have been omitted, and certain vertical dimensions have been exaggerated. In the example of FIG. 9, the base surface 20 of each of the wells 16 includes an upwardly extending support or spacer 88 having an upper end 90 that abuts the bottom portion 28 of the corresponding insert 22. Each spacer 88 has a length 91 sized such that the spacers 88 maintain the membrane 30 at the desired distance D from the base surface 20 of the corresponding well 16. In all other respects, the insert 22 and the well 16 may be similar to those items described above, with the exception that the column may be linger than the depth of the well 16.

Figure 10:
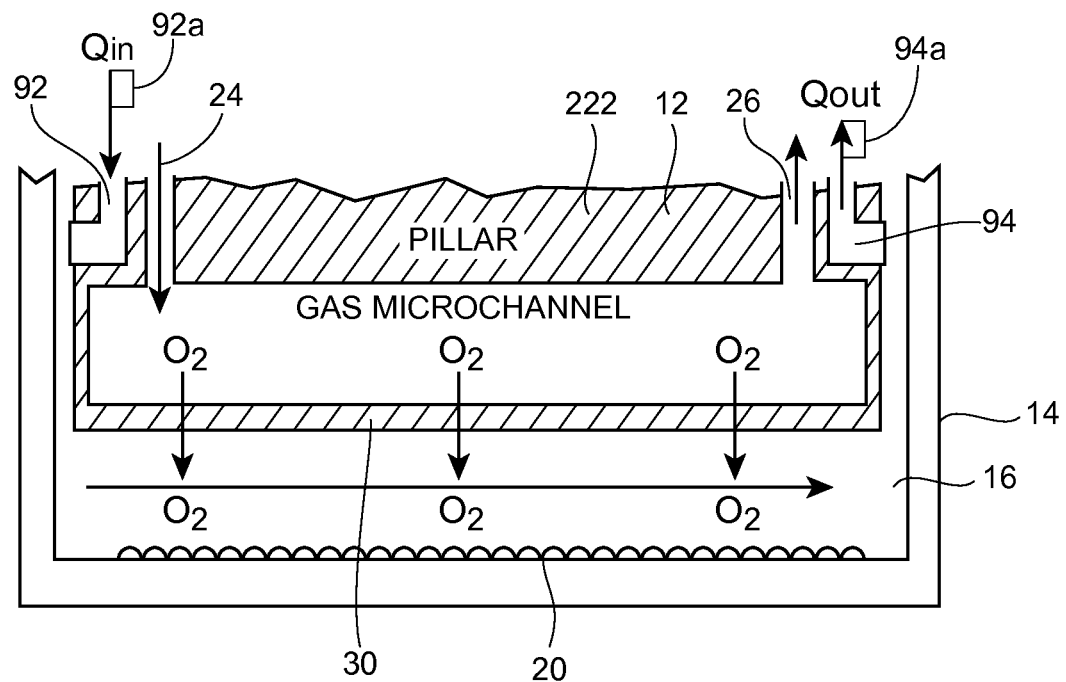
FIG. 10 is an enlarged fragmentary cross-sectional view similar to FIG. 3 and showing still another alternative embodiment in which the insert also includes media supply and exhaust ports.
Figure 11A:
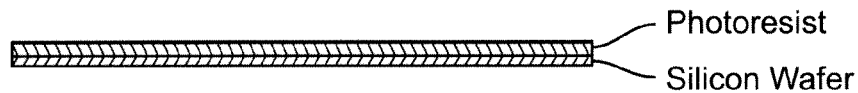
FIG. 11A through 11E show exemplary steps for the fabrication of the inserts of the insert plate.
Figure 11B:
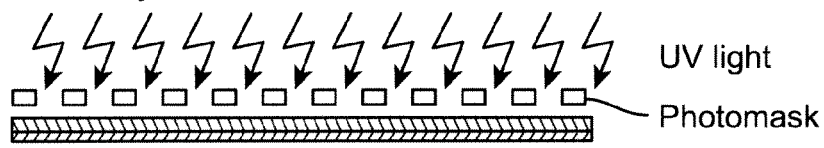
Figure 11C:
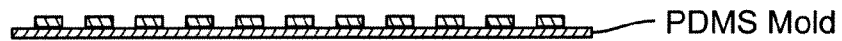
Figure 11D:
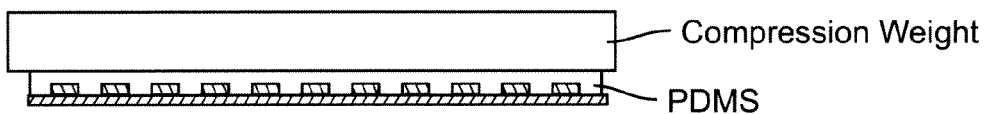
Figure 11E:
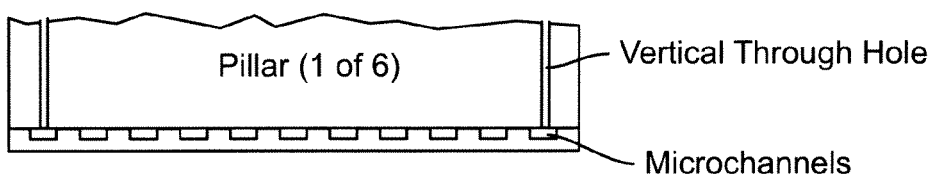
Figure 12B:
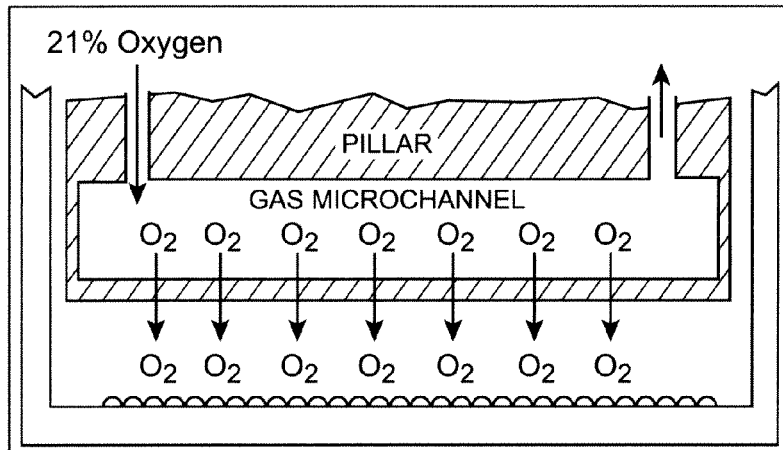
FIG. 12B is an enlarged fragmentary cross-sectional view taken through the insert and well indicated by the circumscribed portion of FIG. 12A.
Figure 12A:
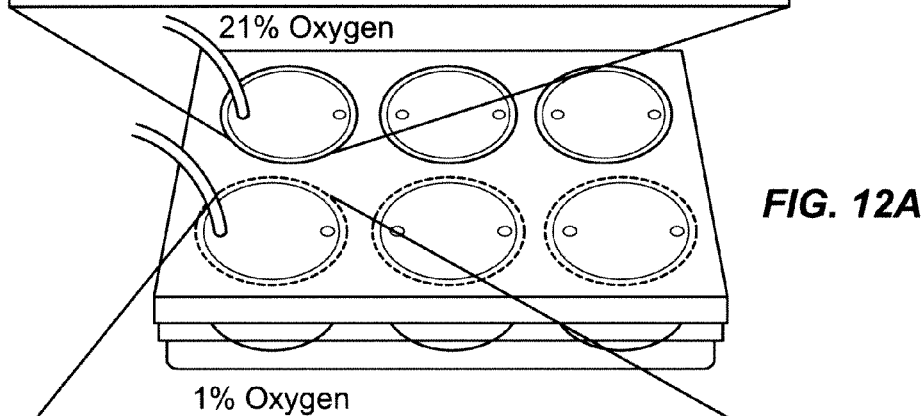
FIG. 12A is a perspective view illustrating two inserts connected to different supply sources.
Figure 12C:
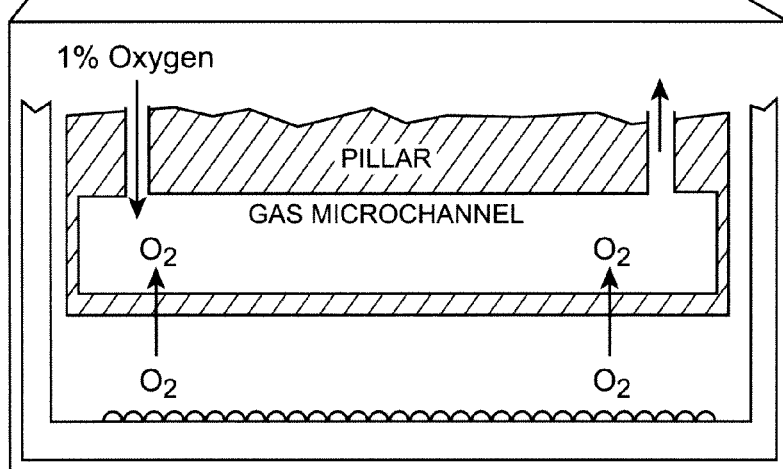
FIG. 12C is an enlarged fragmentary cross-sectional view taken at through the insert and well indicated by the circumscribed portion of FIG. 12A.
Figure 13:
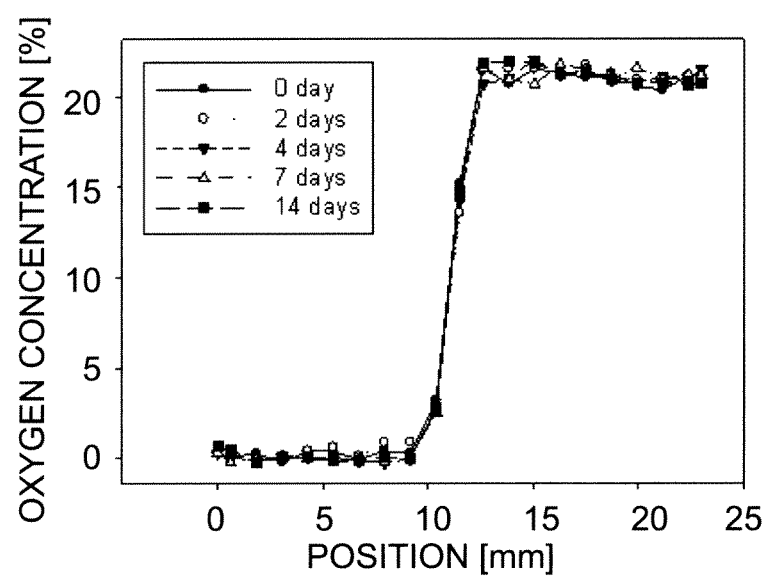
FIG. 13 shows oxygen concentration (%) as a function of the position of a well fitted with an insert having two gas flow channel and two gas sources (21% oxygen and 0% oxygen). The oxygen concentration as a function of position remains constant over the 14 day exposure, indicating that lateral diffusion of gas is negligible.

Referring now to FIG. 10, still another alternative construction is shown. In the example of FIG. 10, an exemplary insert 222 includes the supply port 24, the exhaust port 26, the bottom portion 28, the membrane 30, and the flow channel 32 as described above. The insert 222 includes a separate media supply port 92 and a media exhaust port 94 that are in flow communication with one another through the well 16. The media supply port 92 may be in flow communication with a media supply source via a media supply manifold 92a, while the media exhaust port 94 may be in flow communication with a media exhaust manifold 94a. The manifolds 92a and 94a are shown schematically. Preferably, the media supply and exhaust ports 92, 94 are connectable to their respective manifolds 92a or 94a via flexible tubing or other suitable connections. Consequently, the media within the wells 16 can be controlled in a manner to be described in greater detail below with respect to the quantitative examples. The media may be any solvent, liquid, gas, or any other suitable vehicle.

Quantitative Fabrication Example I

A new silicon wafer was initially cleaned with an acetone and methanol rinse, followed by a rinse in isopropanol. The wafer was dried using $N_2$ gas. The wafer was then exposed to oxygen gas plasma in a microwave plasma system at 50% power for 30 seconds to burn off any residual material on the wafer. The wafer was heated to 130° C. on a hot plate to evaporate any water droplets on the surface. The wafer was then centered on the precision spinner. HMDS was added to the surface to enhance adhesion of the SU-8 photoresist to the wafer. HMDS was spun initially at 500 RPM for 10 seconds for ramp-up and then 6000 RPM for 60 seconds to spread the 50 µl droplet evenly across the surface of the wafer. SU-8 2150 was then added to the surface of the wafer so that approximately half the surface was covered with photoresist. The SU-8 was spun at 500 RPM for 10 seconds for ramp-up, and then 2000 RPM for 30 seconds, to yield a thickness of 300 µM. Following spinning, the wafer was placed on a 65° C. hot plate and warmed for 7 min. The same plate was then heated to 95° C. for soft-baking for 45 min. The wafer was then cooled on the same plate to 65° C. The photoresist-covered wafer was then removed from the plate, and then placed under the UV exposure apparatus. Exposure energy required for 300 µm is 400 mJ/$cm^2$. The photoresist was exposed to UV light through a photomask containing the features for the device channels (see photomask features section for more detail). The wafer was then placed on the 65° C. hot plate and warmed for 5 min. The wafer was then post-exposure baked for 20 min at 95° C., and then cooled to room temperature. The uncrosslinked features of the photoresist were then removed by immersing the wafer in SU-8 developer for 20 min with gentle agitation. The wafer was immediately rinsed with isopropanol following development. Finally, the wafer was heated to 80° C. for 1 h to enhance cross-linking.

PHOTOMASK FEATURES: A photomask was used to fabricate the SU-8 photoresist master. The mask contains an elliptical channel (modified from hexagonal for better $O_2$ flow; 24 mm length×22 mm width) with 300 µm diameter posts to prevent the oxygen permeable membrane from collapsing. The spacing between posts in the current design may be 1.6 mm, although other spacings may prove suitable. In this example, note that the master contains holes where the posts are, because ultimately PDMS will be used for the device and is molded in the master.

FABRICATION OF THE "CHANNEL" COMPONENT: The "channel" or flow channel part of the insert may be considered the part of the oxygen device insert containing the channel features molded with PDMS using the above SU-8 master. First, the finished master wafer was adhered to the bottom of a Fisherbrand 100 cm Petri dish using an evenly distributed ring of double-sided tape near the periphery of the wafer. Strong and even attachment of the wafer is critical to minimize PDMS entry under the wafer and subsequent tilting, which would ruin the height uniformity in the device. Once taped, 12.5 g of mixed and degassed PDMS was poured on top of the master and cured for 2 h at 80° C., yielding an overall height of 1.9 mm (subject to change based on device revision). The cured PDMS remained on the wafer until device final assembly.

FABRICATION OF THE "MEMBRANE" COMPONENT: From here on, the "membrane" component describes the ~100 µm thick membrane in which oxygen will diffuse through in the final device. A reclaimed wafer was cleaned using a new razor blade to remove visible features, and then in alcohol solutions as previously described until the surface was optically spotless. The wafer was then heated at 130° C. to evaporate any water droplets on the surface. Note that using a reclaimed wafer without oxygen plasma was used to minimize adhesion of the PDMS to the wafer upon curing. Silanization yields the same result but was not used in case of biocompatibility issues with the cells. This will be confirmed later. The wafer was then removed and centered on top of the spinning platform. 6 g of mixed and degassed PDMS was poured on top of the wafer. Note that PDMS degassing time after mixing was set to a constant 45 min, because PDMS viscosity increases with increasing curing time, which would affect thickness after spinning. PDMS was then spun atop the wafer at 500 RPM for 10 and then 900 RPM for 30 s. Initial studies confirmed that this spin speed and time yielded a PDMS membrane height of 105±5 µm (will not change). Following spinning, the wafer containing PDMS was heated for 2 h at 80° C. for curing.

FABRICATION OF THE "INSERT" COMPONENT: From here on, the "insert" component describes the PDMS molded from the 6-well block. Plastic weigh boat flat sections were cut and taped to the side of the mold to create a barrier. 126 g of mixed and pregassed PDMS was then poured into the mold so that the overhanging well lip thickness was about 5 mm thick. Too thin of a lip promotes tearing of the well posts from one another, and too thick of a lip makes insert of the device into the wells of the plate for experimentation more difficult due to reduced flexibility. The PDMS was then cured in an oven heated to 80° C. for 3 h. The height of the insert well post is 17.75 mm, plus the additional 5 mm of the lip (subject to change).

BONDING OF DEVICE COMPONENTS: Once all three components (insert, membrane, and channel) were cured, the insert and channel were bonded together after exposure to oxygen plasma for 10 s at 10% power. This alters the surface chemistry of the PDMS to yield irreversible binding. The two materials were carefully pressed against each other and allowed to bond for a minimum of one hour (overnight is best). Then, tubing inlets and outlets were punched using a 3.175 mm diameter hole-punch, extending from the top surface of the insert component to the bottom of the channel component. This was done for each well post channel. Care must be taken to ensure the punch is straight and does not poke through the side wall of the well post. Once the inlets and outlets were punched, the insert/channel component needed to be bound to the membrane component. Both surfaces to be bonded were again treated with oxygen plasma for 10 s at 10% power. Note that the membrane is still on the wafer to ensure that it is flat. Once $O_2$ plasma treated, the insert/channel component was placed on top of the membrane to allow bonding for a minimum of one hour. Then, a circle surrounding the post was cut in the PDMS membrane with a razor blade. The membrane, bound to the insert/channel component, was then peeled off the surface. More precise trimming of membrane was required to get a nice, clean-cut post after removal from the wafer. Finally, six (6) 100 µm thick, 2 mm diameter glass posts were bonded to the periphery of the well posts using the oxygen plasma treatment methods previously described. The thickness of the rigid posts determines the height of the membrane above the bottom of the well (will not change). With the current iteration, the overall thickness of the device from the bottom of the membrane to the top of the lip is 19.8 mm (subject to change).

CLEANING AND PREPARATION OF THE DEVICE: After experimentation, the well posts were immediately immersed in DI water to rinse away any media residue. Once dried, the device was autoclaved for sterilizing. PDMS can be autoclaved using typical parameters hundreds of times without warping or other damage. UV exposure (ie with a culture hood UV light) is also possibility for sterilization, although this was not tested in our lab. The device was carefully wrapped in aluminum foil, placed in a Pyrex container, and then autoclaved. The device was not removed from the container until immediately before experimentation and only in the culture hood.

APPLICATION OF THE DEVICE: Fibroblast cell proliferation experiments were conducted using the oxygen device in our lab. Briefly, the device was carefully placed into the 6-well plate with seeded cells. The flexibility of the device makes it easier to avoid bubbles forming on the membrane surface. Once secured, the assembly was placed in a humidified, $CO_2$-buffered incubator. A small amount of weight was placed atop each well post to ensure contact of the glass posts with the bottom of the well. In future iterations of the device, weights will be incorporated in the device. Tubing leading from the channels of the device were passed through a hole in the wall of the incubator (covered during experiment) and connected to an array of stop-cocks depending on the needs of the experiment. For example, sometimes duplicates were needed so the same oxygen tank was used to provide $O_2$ to two wells. In this case, a stop-cock array was used to split the flow of oxygen. The stop-cocks were linked to a gas flow regulator that allowed precise control of gas to the device. This regulator was attached to the gas tank(s) itself.

Quantitative Fabrication Example II

Device Fabrication: The PDMS device was fabricated in two steps. First the insert array is cast off a Delran mold prepared by standard machining and milling. Next the gas channels were designed in AutoCAD and printed onto a high resolution (5080 dpi) transparency. This transparency was used as a photomask to selectively crosslink a photoresist which is spin coated onto a silicon wafer at a desired thickness (the spin velocity and time dictate the thickness). Following exposure, the unexposed, uncrosslinked photoresist was washed away and the result was a negative mold of the desired channel network. Next, PDMS was mixed from a kit (sylgard 184, Dow Corning) in a 10:1 ratio of prepolymer to crosslinker. This was poured on to the negative mold and cured (80° C. for 60 minutes). This procedure is inexpensive, simple, and termed 'rapid prototyping' as designs can be turned from concept to prototype in under 24 hours which facilitates rapid design iterations when optimizing microfluidic devices. A generalized process flow is shown in FIG. 7.

The microfluidic channels (i.e., the gas channels 16) are fabricated by compression assisted molding which generates a thin controllable membrane over the features of the SU8 mold master with the thickness of the membrane being a function of the applied pressure and SU8 area (Eddington et al., *Journal of Microelectromechanical Systems* 13(4): 586-593 (2004)). These were sectioned into 5 mm circles with a #5 cork borer, and irreversibly bonded to the surface of each insert with oxygen plasma. To decouple the number of gas tubing connecters needed from the number of inserts oxygenated, a microfluidic gas routing manifold was used to evenly distribute the gas from a single inlet to every pillar of the network. This routing network was situated on the topside of the multiwell insert and the single inlets were connected to oxygen sources (mixed gas cylinders, AIRGAS). The gas traveled from the top microfluidic network to the bottom microfluidic network via vertical through holes created during the molding process of the pillar structure.

As shown in one or more of the above-described Figures, the gas channels were separated from the fluidic media of each well by a thin gas permeable membrane, diffusive transport is the only mechanism delivering oxygen to the well. As the diffusion distance is about 200 µm and $D_{oxygen}$ in PDMS≈$D_{oxygen}$ in water, the diffusion times can be calculated and steady-state gradients through the depth of the well are calculated to develop. The gas sources used were 5% $CO_2$ to buffer the media as PDMS is also permeable to $CO_2$. These mixtures were either purchased premixed or mixed on site using a rotometer prior to attachment to the platform. When the concentration of oxygen delivered through the gas network is higher than atmospheric oxygen tension (21%) oxygen is driven into the well (acts like an oxygen source) and when oxygen is below atmospheric oxygen tension, oxygen is extracted from the well (acts as an oxygen sink). After equilibration which requires approximately one minute, steady state tensions were achieved. Additionally the power of scale is leveraged as the gas microchannels act as an infinite sink or source due to the flow rate of oxygen through the gas microchannels at hundreds of mL/minute exchanges the 1 µL volume of the gas reservoir over 1600 times per second.

Quantification: The oxygen tension within each well is characterized using planar and soluble oxygen sensors (FOXY-SGS, Ocean Optics) which contain a ruthenium complex whose fluorescence is quenched in the presence of oxygen as previously described (Carraway, et al. *Analytical Chemistry* 63(4): 337-342 (1991)). The fluorescence intensity can be directly correlated to the oxygen tension via the Stern-Vollmer relationship. Additionally, 2-photon microscopy and soluble oxygen fluorescence sensors are applied to quantify the oxygen concentration throughout the volume of an entire well. Additionally, the oxygen concentration within the incubator is measured using an oxygen probe (FOXY, Ocean Optics) during the course of a standard biological experiment (2 weeks) to determine if the platform alters the global oxygen concentration. Initial experiments indicate this does not occur, but directly measuring the $CO_2$ will eliminate any uncertainties of this.

Membrane Deflection: Membrane deflection under the pressure of gas flowing through the microchannels was addressed as well. Specifically, the deflection of the membrane as a function of membrane thickness (100, 170, and 230 µm) and gas flow rates was quantified under flow rates varying from 0-250 mL/min which corresponds to the experimental range of oxygen flow rates used with this device. Gas was injected into the pillar array and the device was imaged on its side under an inverted microscope and deflection of the membrane was quantified with ImageJ. The maximum deflection of the membrane in these studies was found to be 25 μm for the thinnest membrane at the highest flow rate. As the membrane is preferably fixed approximately 100 μm from the substrate of the well, this deflection foes not influence the monolayer of cells cultured at the bottom of the well. This membrane deflection was minimized by incorporating 100 μm cylindrical support pillars (the protrusions 64) spaced 500 μm which bond the membrane to the top of the microfluidic gas channels as shown in the Figures. Without these support structures, the membrane deflection would be too great and the membrane would contact the substrate of the well.

Oxygen Across Each Well: The oxygen concentration across a single well exposed to a single gas concentration (0%, 10%, and 21%) and a single well exposed to a step gradient of oxygen concentrations (half 21% and half 0%) as shown in FIG. 15. In application, the gas concentrations may vary from about 0% oxygen to about 100% oxygen. The single oxygen concentration experiment was repeated three times with standard deviations shown in FIG. 15B and the step gradient experiment (FIG. 15D-F) was performed one time, but was monitored for 14 days to determine the stability of the imposed oxygen conditions. Combined, these experiments demonstrate the platform generates stable and repeatable profiles over two weeks. The experimental data was acquired with a ruthenium coated substrate (FOXY-SGS, Ocean Optics) which has a fluorescence that is quenched in the presence of oxygen. These fluorescence images can be quantified into actual oxygen tensions via the Stern-Vollmer equation. For these experiments, the platform was docked to a 6-well plate and 1 mL of cell culture media was added to each well and the whole platform was placed in a standard incubator at 37° C. to simulate an actual experiment. The stability of the gradient over 14 days demonstrates the absorption of small amounts of cell culture media does not alter the oxygen diffusivity of the PDMS membrane. This is important as PDMS will absorb hydrophobic small molecules and verifying that this does not alter the transport of oxygen was a welcomed result. In addition to demonstrating the device can modulate the oxygen tension in a well, the device also demonstrates that several oxygen conditions can be established in a single well which is not possible using current techniques.

Figure 15C:
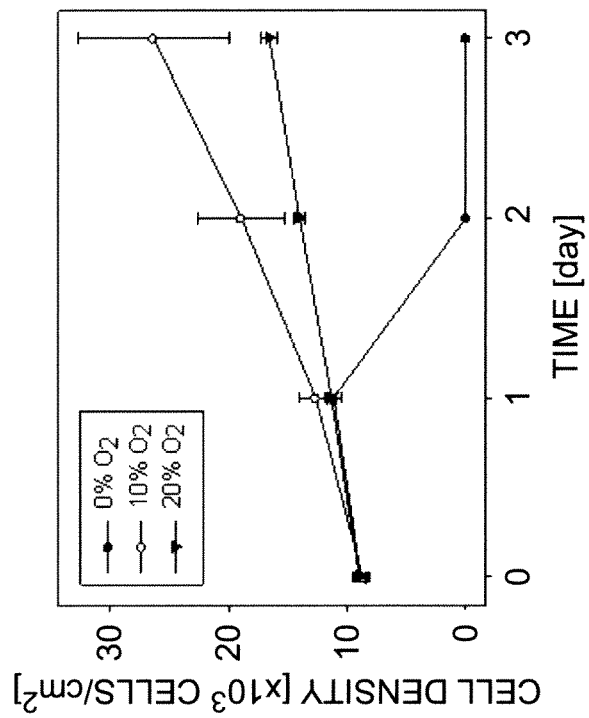
FIG. 15C shows cell density as a function of time for wells exposed to three different oxygen concentrations.
Figure 15A:
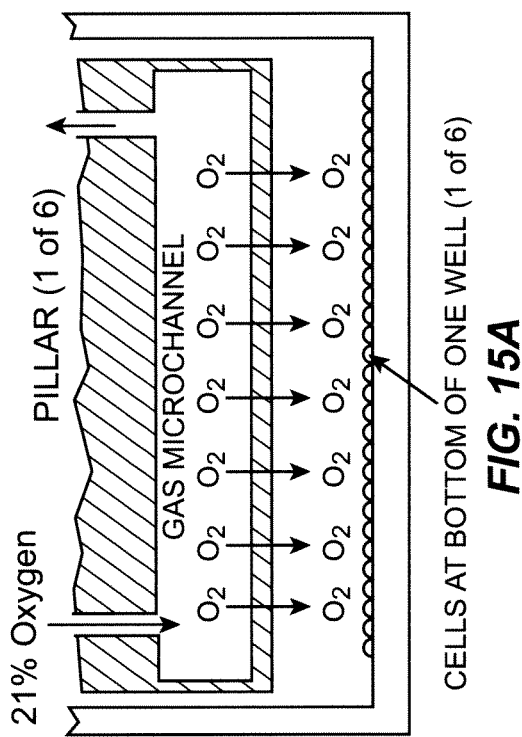
FIG. 15A shows a schematic of a wetted with a device having one gas channel and exposing the well to oxygen at 21%.
Figure 15B:
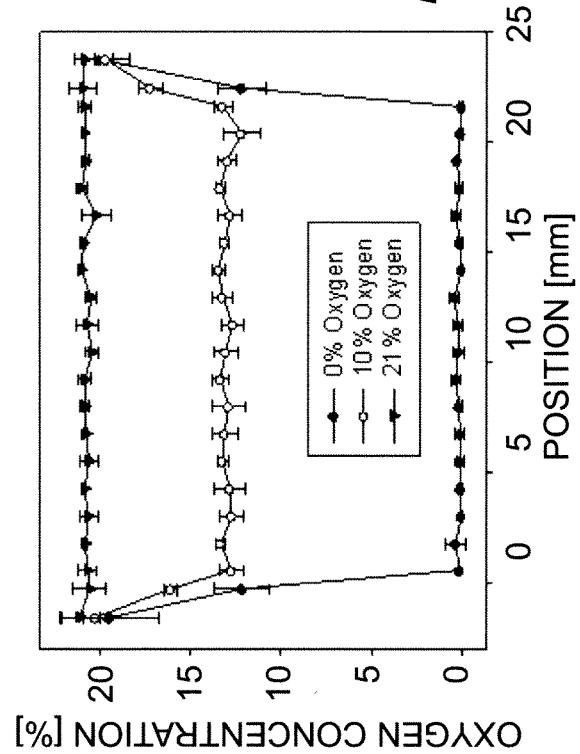
FIG. 15B shows the oxygen concentration measured as a function of position across the well for three different oxygen sources, indicating that the oxygen concentration is constant across the well, with little diffusion.

Cells Cultured: Human dermal fibroblast cells (HDFa) were obtained from Sciencell and were expanded and cultured in accordance with standard protocols as a proof-of-concept that standard cell lines were compatible with the platform. HDFa cells with passage number between 3 and 5 were trypsinized, pelleted, and resuspended in 1 mL of complete media for counting and resuspended to yield a concentration of $1 \times 10^4$ cells/ml. Next, 1 mL of cell suspension added to each well of the 6-well plate ($1 \times 10^4$ cells/well). These plates were used to demonstrate standard cell lines can be cultured and their behavior modified through oxygen delivery and extraction with the platform. Individual wells of a 6-well plate containing HDFa cells were exposed to four oxygen conditions: 21%, 10%, 0% (FIG. 10C), and a 21% to 0% step across one well (FIG. 15F) and cell numbers were tracked over four days (after four days the cultures became confluent) and repeated three times as shown in FIG. 15C. The growth of these cells was directly correlated to the oxygenation conditions of the well in agreement with previous reports (Rosen, et al. *Exp Eye Res* 53(5): 597-601 (1991)). The cells die in lack of oxygen, proliferate under 21% oxygen, and proliferate the most under 10% oxygen. The standard deviations are small for the 21% oxygen as compared with the 10% oxygen. The step 21%-0% shows that new experimental conditions can be easily applied that would be difficult to achieve using standard techniques. This experiment split a single well into two separate oxygen concentrations. It is also important to note the monolayer of cells was consistent across the entire well (except the step condition) pointing to the metabolic depletion of the media was not a factor. These experiments serve as a demonstration that the platform can be used in conjunction with standard cell protocols and cell lines to achieve high throughput and novel experimental possibilities within standard multiwell plates.

BioMEMS and Cell Culture

Bio-MicroElectroMechanical Systems, or BioMEMS, are devices containing micrometer-sized structures fabricated from methods known in the microelectronics industry. A select few applications of bioMEMS include sensors (Beebe, et al. *Nature* 404: 588-590 (2000)), protein crystallization devices (Li, et al. *Proc Nat Acad Sci USA* 103(51): 19243-19248 (2006); Anderson, et al. *Biochemistry* 46(19): 5722-5731 (2007)), micro total analysis platforms (Reyes, et al. *Analytical Chemistry* 74(12): 2623-2636 (2002)), devices to measure cell mechanics (Tan, et al. *Proc Nat Acid Sci USA* 100(4): 1484-1489. (2003)), chemical synthesis chips (Lee, et al. *Science* 310(5755): 1793-1796 (2005)), and genetic analysis platforms (Marcus, et al. *Analytical Chemistry* 78(3): 956-958 (2006); Ottesen, et al. *Science* 314(5804): 1464-1467 (2006)).

Due to the high precision in creating structures on the same scale as cells, many physiological processes can be more precisely studied such as the effect of temperature on a developing drosophila embryo, which would be difficult to do using traditional techniques (Lucchetta, et al. *Nature* 434 (7037): 1134-1138 (2005)). One of the earliest examples of bioMEMS analyzed how cell size influences proliferation and is independent of the amount of focal adhesion contact between the cell and the substrate (Chen, et al. *Science* 276 (5317): 1425-8 (1997)). This experiment was not possible with traditional techniques and demonstrates how bioMEMS facilitates advancement in biomedical knowledge through new experimental modalities.

Oxygen and Cell Culture

Oxygen is a key metabolic variable that influences many different biological phenomena. However, current tools to probe this variable are crude and inefficient, and have not changed since the onset of cell culture techniques. The hypoxic chamber remains the tool of choice, and has been used substantially in applications requiring control over the oxygen tension exposed to cells.

However, the hypoxic chamber fails to satisfy the needs of biomedical researchers to efficiently modulate oxygen tensions over multiple conditions because a separate hypoxic chamber is required for each condition. Research into oxygen-implicated biological pathways, such as hypoxia-inducible factor (HIF) family of heterodimeric transcription factors regulate the cellular response to oxygen tension (Wang, et al. *Proc Nat Acad Sci USA* 92(12): 5510-5514 (1995)), would benefit from a means of providing a variety of oxygen conditions. HIF-1α is a ubiquitous transcription factor that plays a role in development (Haddad *Cytokines Cellular & Molecular Therapy* 7(1): 1-14 (2002)), solid tumor growth (Kondo, et al. *Cancer Cell* 1(3): 237-246 (2002)), and angiogenesis (Maxwell et al., *Seminars in Cell & Developmental Biology* 13(1): 29-37 (2002)), and providing a simple tool to explore HIF-1α would greatly facilitate these investigations and accelerate scientific discovery.

In addition to increasing the throughput of hypoxic experimentation, the present invention has a potential to facilitate new experiments not possible with current techniques. Gradients of oxygen are standard byproducts of cellular metabolism found throughout every tissue and across all organisms.

Gradients of oxygen are increasingly highlighted as crucial metabolic regulators when studying drug toxicity (Lin et al., *Clinical Pharmacokinetics* 35(5): 361-390 (1998); Allen, et al. *Hepatology* 38(4): 270a-270a (2003)), the hematopoietic stem cell niche (Parmar, et al. *Proc Nat Acad Sci USA* 104 (13): 5431-5438 (2007)), plant biology (Drew *Annual Review of Plant Physiology and Plant Molecular Biology* 48: 223-250 (1997); Alvarez, et al. *Cell* 92(6): 773-784 (1998)), liver zonation (Holzer et al, *J Cell Physiol* 133(2): 297-304 (1987); Allen et al, *Biotechnology and Bioengineering* 82(3): 253-262 (2003)), and throughout developmental biology (Harvey *Animal Reproduction Science* 98(1-2): 113-128 (2007); Uno, et al. *Developmental Dynamics* 236(4): 981-990 (2007)). Thus replicating these in vivo gradients in an in vitro model accessible to any standard cell biology lab would have a substantial impact across many fields. One such example is recreating the hematopoietic stem cell niche because recent studies have demonstrated the interaction of stem cells with their bone marrow microenvironment is a critical process in maintaining normal hematopoiesis. The progenitor cells and the supporting cells of the stem cell niche are predominantly located at the lowest end of an oxygen gradient in the bone marrow with the implication that regionally defined hypoxia plays a fundamental role in regulating stem cell function. The present invention can replicate these in vivo oxygenation gradients in an easily accessible method to study hematopoiesis. In addition to in vitro models, a device disclosed herein can be used to address clinically relevant problems, for example, transplantation cells and tissue can benefit from a more controlled oxygen environment. For example, islet transplantation (an experimental therapy for insulin dependant diabetes) involves harvesting islets of Langerhans from donor pancreas and transplanting into the vasculature of the liver. The islets are highly vascularized in vivo, and hence, once removed from its supportive stroma are highly susceptible to the hypoxic conditions present during isolation and prior to implantation (Giuliani, et al. *Cell Transplant* 14(1): 67-76 (2005)). Thus, the disclosed devices can be used to provide a more favorable culture condition and can help to solve a current unmet clinical and experimental need.

In accordance with the disclosed example, the device disclosed herein may improve currently available oxygen modulation systems by increasing the throughput of investigations without sacrificing experimental simplicity. The device further may enable seamless integration into any biomedical research laboratory equipped with standard materials (multiwell plates, gas cylinders, and incubators). These devices and methods allow the researcher to explore the effect on various and well controlled gas concentrations, which can be desirable to research areas, such as hypoxia, an as yet largely ignored metabolic variable in cell biology.

The majority of cell biology is conducted in incubators set to 21% $O_2$ and 5% $CO_2$. However, gradients of oxygen are found throughout all biological systems and are difficult to replicate under these conditions. The disclosed devices and methods reduce or eliminate experimental barriers to impose oxygen gradients in standard cell culture materials to improve cellular assays. The device is modular and can be used in conjunction with a multiwell plate, which typically is found throughout biomedical research labs. The device requires no special equipment or training to operate. The device disclosed herein provides a new in vitro high-throughput tool capable of probing a previously difficult to control variable (e.g., gas concentration) and enhances experimental efficiency.

A present device has a plurality of inserts matching the number and spacing of individual wells of the multiwell plate that it is designed to nest into (e.g., 6, 24, or 96-wells). Oxygen flow through the flow channel 32 at the base of each insert 22 is separated from the fluidic contents of the well 16 by the gas permeable membrane 30. The flow channel is connected to a gas source which provides the pressure to deliver the gas throughout the device. The device can act as a sink or source of a gas of interest, e.g., oxygen, depending on the concentration of the gas in the gas channels. The gas is delivered to the well through simple diffusion of the gas across the gas-permeable membrane and the reaction medium (e.g., buffer, solvent, and the like). The reaction in the well, e.g., cultured cells, are never in contact with gas and hence issues with gas bubbles disrupting the integrity of e.g., the cell membrane can be avoided.

PDMS may be preferable for the membrane 30 because of its optical clarity, gas permeability ($D_{oxygen}$ in PDMS=$3 \times 10^{-5}$ cm$^2$/s), and ease of rapid prototyping. However, several recent studies have highlighted the ability of PDMS to absorb water and hydrophobic soluble factors (Randall et al., *Proc. Nat. Acad. Sci. USA* 102(31):10813-10818 (2005); Roman, et al. *Analytical Chemistry* 77(5):1414-1422 (2005); Heo, et al. I 79(3): 1126-1134 (2007); and Mukhopadyay I 79(9):3248-3253 (2007)). Thus, in some embodiments, the inserts 22 may be made of a material different from that of the gas-permeable membrane. Examples include other polymers more resistant to hydration and absorption such as polymethylmethacrylate (Narasimhan et al., *J Micromechanics Microengineering* 14(1):96-103 2004)), cyclic olefin copolymers [Paul, et al. *Electrophoresis* 28(7):1115-1]22 (2007) or polycarbonates (Ye et al., *Analytical and Bioanalytical Chemistry* 381(4): 820-827 (2005)).

Water loss through absorption into PDMS could be detrimental in cell culture that relies on specific concentrations of solutes to maintain pH and nutrient levels. In embodiments where PDMS is the support material and the gas-permeable membrane, the pillar can be pre-hydrated by soaking in water prior to use or incorporate a microfluidic water jacket layer (Kong, et al., *Nucl. Acids Res.* 35(8): e61 (2007)) in the platform that will accomplish the hydration no as to minimize disruption of the media concentrations used. Additionally or alternatively, the media inlet and media outlet can be used to exchange the culture media which will offset fluid loss through absorption.

The flow channels may be fabricated through standard soft lithographic techniques (Duffy, et al., *Analytical Chemistry* 70: 4974 (1998)) and the insert array may be fabricated through casting a support material into a machined mold. In some embodiments, the support material and the gas-permeable material are the same material. In other embodiments, the support material is different from the gas-permeable material.

Device Options

Six different versions of the device are described, in increasing complexity: Version I—independently vary the oxygen concentration within each well of a 6-well plate; Version II—impose gradients of oxygen across each well of a 6-well plate; Version III—incorporate perfusion into Version I and II; Version IV—independently vary the oxygen within each well of a 96-well plate, Version V—incorporate micropatterned multiwell plates to dock with Versions I-IV, and Version VI—adapt the platform to a MEA culture chamber.

Version I: Independently Vary the Oxygen within Each Well of a 6-Well Plate

The first iteration demonstrates the ability of the device to control the oxygen concentration within each well of a 6-well plate independently of the global incubator condition. Version I is designed with each row of the 6-well plate to have a different oxygen condition (2 sets of 3 wells). This simplifies the routing of the gas lines as only 2 inputs (one for each row) are required for these experiments. Several platforms can be connected serially or in parallel to increase the throughput of experimentation. As the platforms and connecting tubing is housed in a standard incubator with 5% $CO_2$, the $CO_2$ levels are constant throughout the system and are quantified. Preliminary experiments have demonstrated oxygen can be delivered to a monolayer of cells using this platform and the $CO_2$ effectively buffers the pH of the culture media. However the oxygen profiles were only quantified for a single well over 14 days. These initial experiments are expanded to characterize the oxygen profiles across the entire multiwell plate over a similar time course. If diffusion of oxygen across PDMS significantly alters the oxygen concentration in neighboring wells, the diffusion can be reduced by incorporating a circulating water jacket layer acting as a sink for any meandering oxygen in the bulk of the platform. However, this unintended diffusion can be leveraged by having a gradient of conditions within a single plate. For example if a well is injected with 0% oxygen, the first three wells may be 0%, 1%, and 2% due to oxygen diffusion from the atmosphere. Regardless of the severity of this diffusion, as long as it is characterized and quantified, the device can be adapted to discourage or encourage this phenomena, depending on the end application. In addition to quantifying oxygen concentrations, cellular response to oxygen tension is quantified through standard live/dead assays as well as protein quantification of the hypoxia-inducible factor (HIF) family of heterodimeric transcription factors which regulate the cellular response to oxygen tension (Wang, et al. *Proc Nat Acad Sci USA* 92(12): 5510-5514 (1995)). HIF-1$\alpha$ is a ubiquitous transcription factor that plays a role in development, solid tumor growth, and angiogenesis. HIF-1$\alpha$ is quantified through Western analysis. Previous work has shown the cells used (HDFa) expresses HIF-1$\alpha$ (Li, et al. *Embo Journal* 26(5): 1221-1233 (2007)).

While oxygen rapidly diffuses through PDMS, if the pressure is too high it can also permeate across a cell membrane which would result in bubble formation and experimental failures as the bubbles would damage the integrity of the cell membrane. Thus, the maximum flow rates that can be used without bubble formation is calculated. As the permeation is a function of pressure, the pressure can be reduced in the gas network by reducing the resistance of the gas channels which can be easily accomplished by increasing the height of the channels as the resistance is inversely proportional to the radius of the microfluidic channel and the pressure is directly proportional to the resistance.

Metabolic depletion of the components of the culture media is also of concern. The media volume of the well is identical to standard practices for 6-well plates (1-2 mL), however the insert reduces the amount of media directly above the cells from 1-2 mm to 100-200 µm. This is the primary concern when discussing the platform with potential users. Preliminary experiments suggested that this was not an issue as a consistent proliferation was observed across the well no any evidence of increased cell death in the center of the well (where the diffusion distance is the largest) was observed. Even if this is an inevitable byproduct of the device, it can be leveraged to study the effect of gradients of soluble factors in addition to gradients of oxygen as the potential metabolic depletion will result in a radial concentration gradient with the highest concentration at the edge of the pillar and the lowest at the center. Use of a device (Version III, discussed below) having a media inlet and outlet overcomes this through the incorporation of perfusion across the well to gradually replace the cell media as needed.

The data shows that this device works to control oxygen concentration in a well, cells thrive, and the oxygenation profile is stable over 14 days.

Version II: Impose Gradients of Oxygen Across Each Well of a 6-Well Plate

Figure 15F:
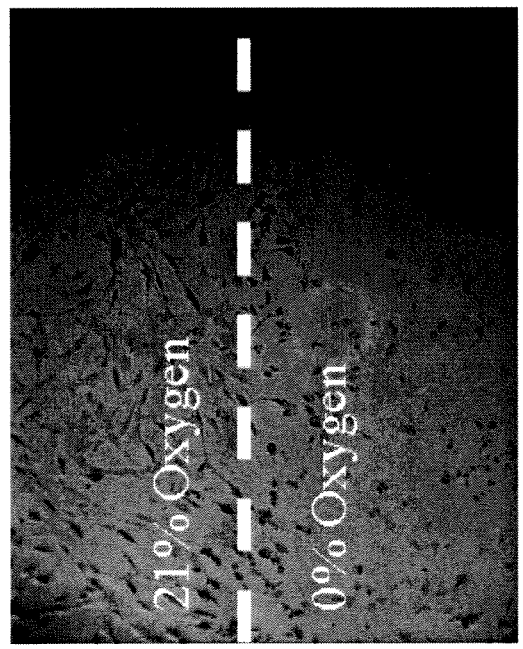
FIG. 15F shows a picture of cells in a well fitted with the device shown in FIG. 15D, showing the cell density is much higher in the portion of the well exposed to 21% oxygen in comparison to the portion of the well exposed to 0% oxygen.
Figure 15D:
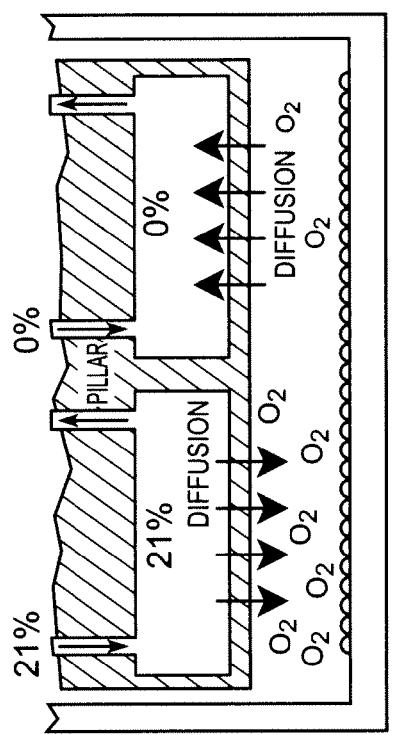
FIG. 15D shows a schematic of a well fitted with a device having two gas channels and exposing the well to two different oxygen concentrations (21% and 0%)
Figure 15E:
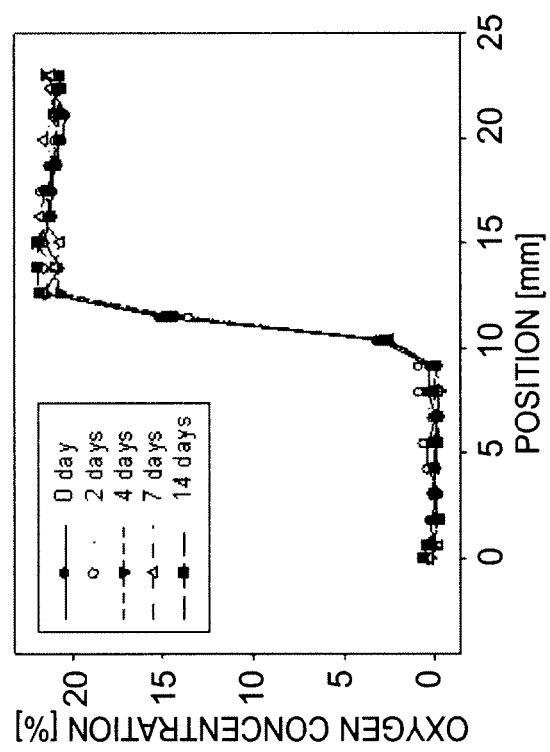
FIG. 15E shows the oxygen concentration measured as a function of position for the well fitted with the device of FIG. 15D, indicating that the oxygen concentration is constant for each portion of the well below each gas channel, with little diffusion between the two portions of the well.

Version I is essentially a high throughput hypoxic chamber and would accelerate the rate of experimentation by allowing more conditions to be tested simultaneously. Version II is built on this with the added functionality of creating steady state gradients across each well which is currently not possible with standard hypoxic chambers. Gradients of oxygen are standard byproducts of cellular metabolism found throughout every tissue and across all organisms. These gradients of oxygen are increasingly highlighted as crucial metabolic regulators when studying drug toxicity, plant biology, and throughout developmental biology. Thus replicating these in vivo gradients in an in vitro model accessible to any standard cell biology lab would have a huge impact across many areas of biomedical research. A schematic of Version II is shown in FIG. 15D. The platform is fabricated, operated, and quantified in the same manner as Version I with the exception that two gas inputs are required to deliver oxygen to each well. Similar to Version I, Version II can be connected serially to increase the number of oxygen concentrations investigated while minimizing the number of gas cylinders required. One important consideration for these studies is lateral diffusion through the PDMS microfluidic network between the gas microchannels. As previously mentioned, this should be negligible as the flow rate of oxygen through the gas chambers at hundreds of mL/minute exchanges the 1 µL volume of the gas reservoir over 1600 times per second. This large flow rate allows for the assumption that the concentration of the gas chambers is constant regardless of whatever trickle of oxygen diffuses through the chambers, as it is dwarfed in comparison to the gas injected through the microchannels with the exception of a transitional region shown in FIG. 15E between the two oxygenation networks. Additionally, a simple step oxygen condition in a single well was demonstrated (FIG. 15D-F). However many other conditions are interesting to demonstrate as shown, such as linear gradients, radial gradients, oscillations across the well and extremes in a single well. The oxygen tension in these devices needs to be quantified, as previously described, above, in addition to demonstrating a cellular response to these interesting profiles. The parameter space of imposing oxygenation profiles at the surface of cell monolayers is probed to determine the design limits such as the maximum number of conditions in a single well, the maximum slope of the oxygen concentration from two adjacent oxygen tensions, and the real issue of connecting the gas microchannels to oxygen sources (maximum number of oxygenation conditions). The preliminary data shows the technique works, cells thrive and respond to the gradient, and the oxygenation profile of the gas channels is translated into the well.

Version III: Incorporate Perfusion into Versions I and II

Version III addresses the previously discussed issue of metabolic depletion of the culture media by incorporating perfusion inlets and outlets to the base of each pillar so the tissue culture media can be exchanged and collected. Typically each well of a 6 well plate contains 1 mL of culture media and this is changed daily. If this volume of media were slowly exchanged over 24 hours this would correspond to a volume flow rate of 0.7 µL/min which can be delivered with a standard perfusion pump connected to the device with each pillar of the insert having one inlet and one outlet for culture media at the base as shown in FIG. 10. When considering convection and diffusion, the Peclet number (Pe=uL/D; where u is the x velocity, L is the characteristic length, and D is the diffusion coefficient) is the dimensionless number comparing the significance of convection and diffusion and shows how many characteristic lengths would be necessary to generate complete mixing (Squires et al., *Reviews of Modern Physics* 77(3): 977-1026 (2005)). For this application, the Peclet number is 3 which corresponds to 1 mm until complete mixing is achieved which implies 1 mm from the edge of the pillar has the same oxygen profile as under static flow, but between the edge and 1 mm, diffusion does not carry the oxygen down fast enough before convection carries it away. Of course these are rough estimates meant to gauge the system within an order of magnitude, and can be subject to more detailed modeling and experimental validation using fluorescent oxygen sensors. However, the flow rate is low enough to allow confidence that the device acts as expected even when considering the simplifications of the calculations.

Additionally, the added functionality of perfusion allows one to analyze shear on cellular systems in addition to oxygen. Shear stress is a crucial component of many cellular systems and mimicking the in vivo shear condition benefits from the high throughput modular inserts as current practices are limited to serial perfusion chambers. However, high shear rates will prevent oxygenation of the media through diffusion and for these studies oxygen can be delivered through oxygenated media as in standard perfusion devices. While high shear studies prevents diffusion based oxygen delivery, it is important to note the high-throughput modality of these studies would be difficult to achieve with standard techniques and is not without merit.

Version IV: Independently Vary the Oxygen within Each Well of a 96-Well Plate

Versions I-III are based on the 6-well culture plate to seamlessly integrate into standard biomedical research lab protocols. The 6-well plate allows sufficient cellular material to run additional characterization assays such a Western blot to quantify presence of proteins indicative of cellular function. However, it is also advantageous to allow studies in higher-throughput formats such as the 96-well plate when in situ fluorescence is sufficient to quantify cellular function. This will allow the disclosed method to merge with current high content screening protocols (Abraham, et al. *Trends in Biotechnology* 22(1): 15-22 (2004)) and increase the broad impact of the device on biomedical research. This version is fabricated and characterized using the same protocols as described above with the exception of having 96 pillars instead of 6. The oxygen tension is validated in all 96-wells using the above-described methods. The cellular response is validated through immunofluorescent imaging of HIF-1α (Risbud, et al. *J Cellular Biochemistry* 98(1):) 152-159 (2006)) as there is insufficient cellular material to run western blots.

Version V: Incorporate Micropatterning into Platform

The fate and function of mammalian cells are influenced by microenvironmental cues including interactions with soluble factors, physical forces (Galbraith et al, *Current Opinion in Cell Biology* 10(5): 566-571 (1998); Tan, et al. *Proceedings of the National Academy of Sciences of the United States of America* 100(4): 1484-1489 (2003)), extracellular matrix (ECM) (Lin, et al. *Tissue Engineering* 10(7-8): 1046-1053 (2004); Flaim, et al. *Nature Methods* 2(2): 119-125 (2005)), and neighboring cells (Bhatia, et al. *Faseb J* 13(14): 1883-900 (1999); Nelson et al., *Febs Letters* 514(2-3): 238-242 (2002).

While the first four versions of the platform are primarily concerned with oxygen delivery, Version-V focuses on precisely controlling the cell-ECM and cell-cell interactions in addition to oxygen. In culture, cell adhesion and spreading can be modulated through interactions with coatings of ECM that act through integrin signaling pathways. Interactions with neighboring cells (both 'homotypic' or 'heterotypic') can mediate their influence through both contact-mediated and soluble signals (Schwartz et al., *Nature Cell Biology* 4(4): E65-E68 (2002)). Traditional tools to address these parameters are limited to bulk manipulations of the culture conditions such as adsorbing ECM components at various densities or varying cell-cell interactions via cell seeding densities (Masur et al. *Proc. Nat. Acad. Sci. USA* 93(9): 4219-4223 (1996)). While these techniques have yielded valuable experimental data and insight, engineering microenvironmental cues through micropatterning enables uncoupling of key variables. Recently, various methods to control cell-matrix and cell-cell interactions through protein and cellular micropatterning have been reported (Khademhosseini, et al. *Proc. Nat. Acad. Sci. USA* 103(8): 2480-2487 (2006)). Some examples include microcontact printing (Singhvi, et al. *Science* 264(5159): 696-698 (1994)), microfluidic patterning (Chiu, et al. *Proc. Nat. Acad. Sci. USA* 97(6): 2408-2413 (2000)), photolithographic patterning (Bhatia, et al. *J Biomed Mater Res* 34(2): 189-99 (1997)), stencil patterning (Folch, et al. *Journal of Biomedical Materials Research* 52(2): 346-353 (2000)), and ink-jet printing (Pardo, et al. *Langmuir* 19(5): 1462-1466 (2003)). However, these techniques often require specific substrates (e.g. gold), are limited to simple geometries (e.g. contiguous patterns) and flat, rigid surfaces (e.g. glass or silicon for photolithography), and cannot be utilized in high-throughput platforms such as multiwell plates. However, version-V implements a method for micropatterning in a standard multiwell plate through selective ablation of biomolecules using oxygen plasma.

Figure 17:
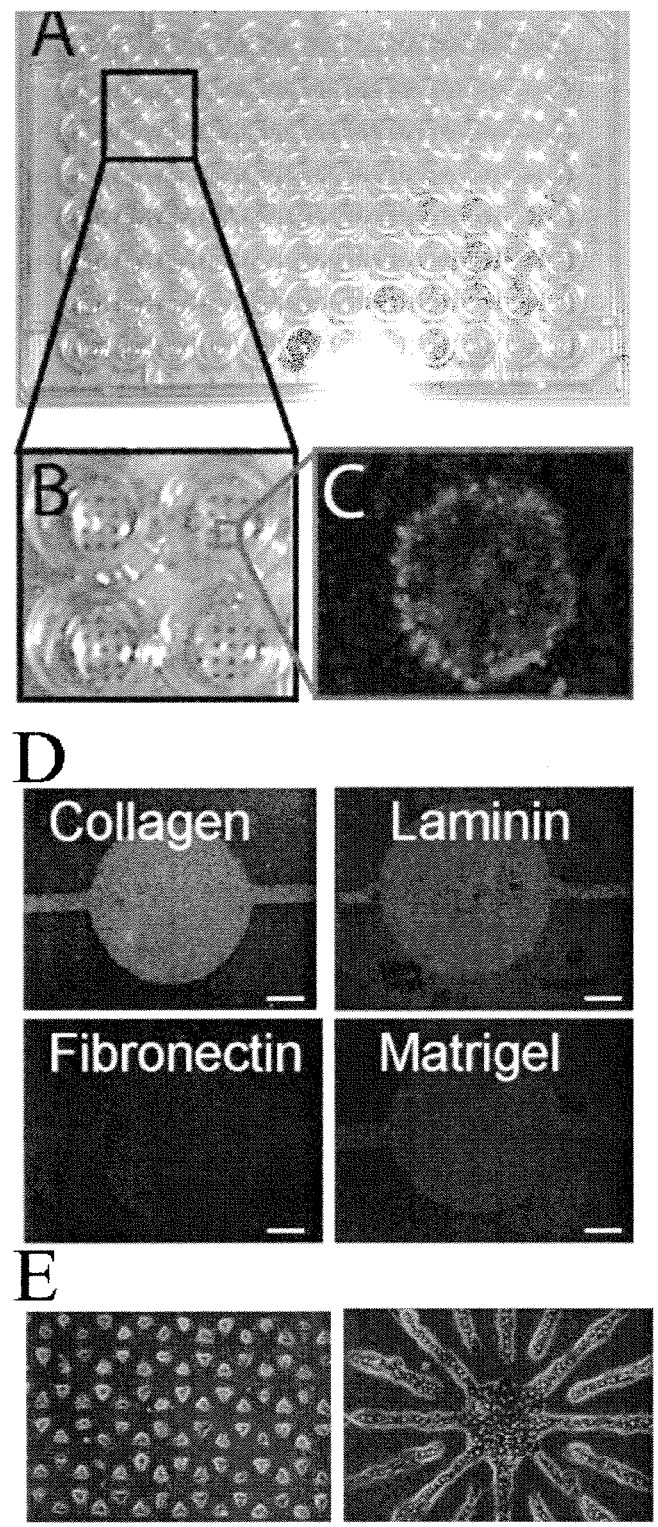
FIG. 17 shows A) Image of a micropatterned 96-well plate with B) 4 wells magnified to better visualize the micropattern and C) fluorescence image showing hepatocyte islands (green) surrounded by fibroblasts (blue). D) fluorescently labeled collagen type-I, fibronectin, lamanin, and Matrigel micropatterned in a 96 well plate. E) Two images of micropatterned cells demonstrating the flexibility in cell patterning.

The technique is conceptually similar to the devices disclosed herein, with the exception of the base of each pillar contains a microtopography instead of an embedded microfluidic channel. The micropatterning is accomplished in two steps. A biomolecule is first physisorbed to the substrate, followed by masking and selective ablation in an oxygen plasma. A microstructured PDMS template is placed in conformal contact with a physisorbed, dried substrate. The regions of the substrate in contact with the PDMS template will be protected from oxidation by plasma and left intact, while the others are oxidized and removed by the plasma. The two main requirements for implementing this technique are: (1) the biomolecule is able to withstand air-drying following adsorption, and (2) the protected material is able to fit inside a plasma system. The technique is adaptable to any oxygen plasma system; however the etching rate will vary with the power and configuration. A sample micropatterned 96-well plate is shown in FIG. 17 and this can simply dock to the oxygenation platform. This can be used to micropattern cells in maximums or minimums of oxygen tension and monitor their behavior as a function of complex oxygen gradients, cell shape, and proximity to neighboring cells. Furthermore, the ECM micropattern can be composed of several different biomolecules to determine the role of oxygen-ECM cross-talk (if any).

Figure 18:
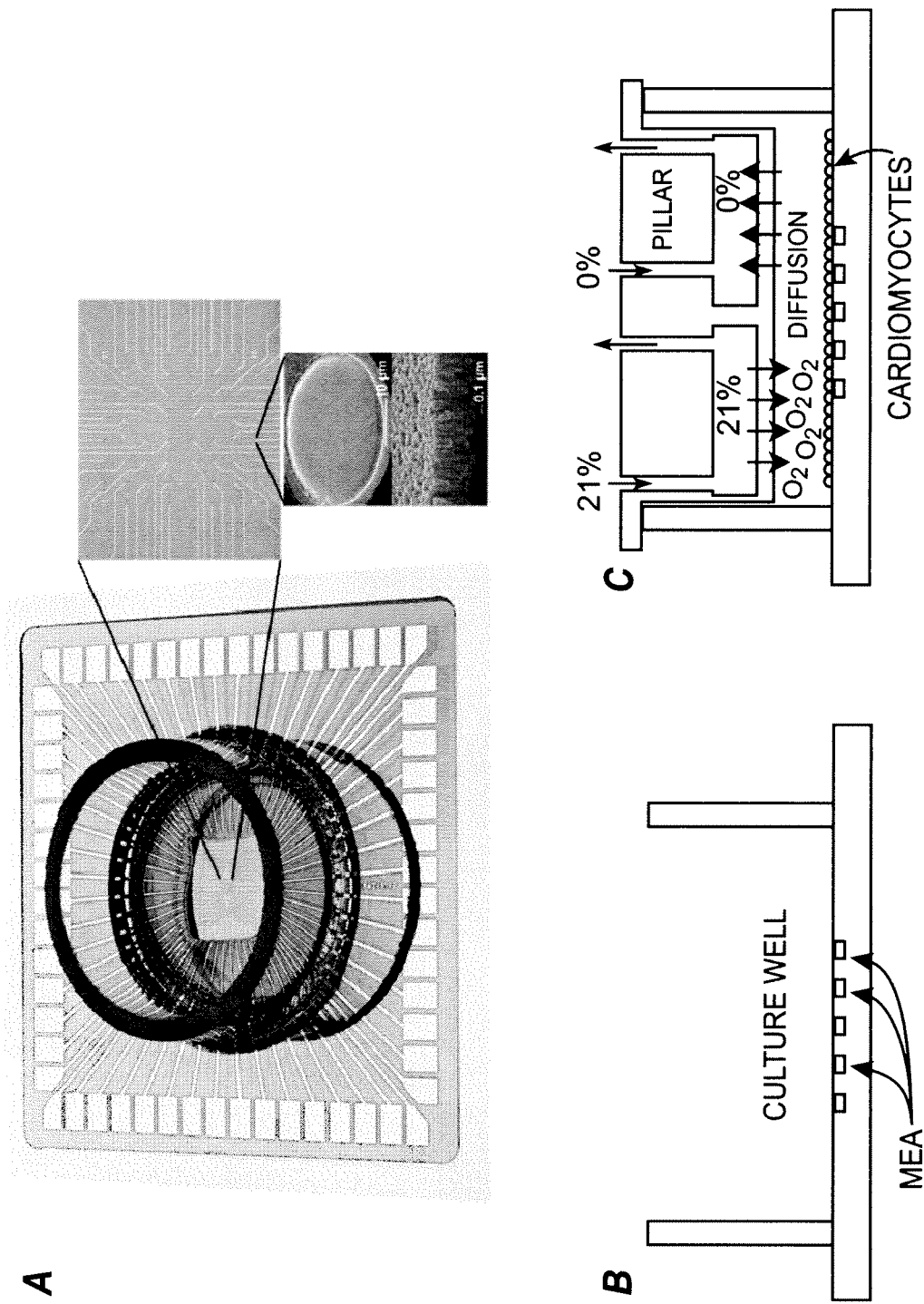
FIG. 18 shows A) a microelectrode array (MEA), available from Multichannel Systems. B) Schematic cross section of the MEA and C) schematic cross section of the MEA with the oxygenation insert depicting a binary oxygen condition imposed on the monolayer of cardiomyocytes cultured on the MEA.

Version VI: Adapt to Impose Oxygen Gradients on a Monolayer of Cells Cultured on an MEA In addition to standard multiwell plates, the device is adapted to dock to a microelectrode array (MEA) as shown in FIG. 18. This will be used in conjunction with a monolayer of cardiomyocytes (HL-1) cultured on the MEA and we can monitor the relationship between hypoxia and ischemic reperfusion injury by monitoring the action potential propagation in the cardiomyocytes as shown in FIG. 18. This allows one to probe the intercellular communication pathways of cardiomyocytes and how they are altered by physiological as well as pathophysiological conditions. Hypoxia changes not only the excitability of the cardiac tissue but also increases the intercellular resistances between the cardiomyocytes thereby leading to a decrease in the conduction velocity of action potential propagation. To understand this phenomenon is of particular importance at the border zone between hypoxic and normoxic tissue where the heterogeneity of the substrate may result in arrhythmic excitations and reentry as shown in FIG. 14. This version allows one to analyze how oxygen modulates propagation of action potentials in autonomously beating cardiomyocytes. Uncoupling these key variables would provide a new and exciting tool to study the relationship between oxygen and action potential synchronization. Specifically, The regions of the cardiomyocytes cultured on the MEA are exposed to hypoxia and others to normoxia and then monitored for how this alters the synchronization of the spontaneously beating cardiomyocytes over various time scales (minutes, hours, and days). In addition, this version allows a screening system that allows the analysis of pharmacological interventions to prevent or treat hypoxia induced tissue damage. The electrodes are spaced 500 µm apart and one can easily control the oxygen within this space over two adjacent electrodes as shown in the preliminary data. The uneven nature of the commercially available pyrex outer ring (fluctuation in diameter is about 50 µm) which may cause a variability in spacing between the insert and the cells cultured in the chamber. This variability can lead to oxygen highs and lows depending on the spacing between the insert and the cells. To overcome this potential obstacle, the ring can either be ground down using standard metallurgical sample preparation techniques (successively smaller grit), or a built ring up using a top layer of PDMS to reduce the variability. This insert is not limited to cultured cardiomyocytes and can be extended to any cell types cultured on MEAs such as neuronal cells (Gross, et al. *Journal of Neuroscience Methods* 50(2): 131-143 (1993); Borkholder, et al. *Journal of Neuroscience Methods* 77(1): 61-66 (1997)) to deliver another class of devices to be easily disseminated to a large biomedical research community.

From the foregoing it will be appreciated that, although specific embodiments of the invention have been described herein for purposes of illustration, various modifications may be made without deviating from the spirit and scope of the invention.

What is claimed:

1. An assembly comprising:
    a multiwell plate, the multiwell plate having a plurality of wells, each of the wells having an opening and a base surface;
    an insert plate, the insert plate having a plurality of inserts positioned to align with a corresponding one of the wells whereby the insert plate can be coupled to the multiwell plate with each insert disposed in the corresponding well;
    each of the inserts including:
        a supply port arranged for flow communication with a supply source;
        an exhaust port;
        a bottom portion;
        a gas permeable membrane secured to the bottom portion; and
        a flow channel formed between the gas permeable membrane and the bottom portion of the insert, the flow channel providing flow communication between the supply port and the exhaust port; and
    wherein at least one of the inserts further includes:
        a second supply port arranged for flow communication with a second supply source;
        a second exhaust port; and
        a second flow channel formed between the gas permeable membrane and the bottom portion of the insert, the second flow channel providing flow communication between the second supply port and the second exhaust port, the second supply port connectable to a second supply source;
    wherein the first flow channel and the second flow channel are separated from one another by a boundary; and
    each of the inserts having a length sized to position the gas permeable membrane a desired distance from the base surface of the multiwell plate when the multiwell plate and the insert plate are coupled to one another.

2. The assembly of claim 1, wherein the bottom portion of each of the inserts is parallel to the base surface of the corresponding well.

3. The assembly of claim 1, wherein the multiwell plate has a support surface and a portion of the insert plate rests on the upper surface, and wherein the length of each of the inserts is sized based on a distance from the support surface to the base surface.

4. The assembly of claim 1, wherein the gas permeable membrane includes a plurality of upwardly extending protrusions, the first and second flow channels extending between adjacent protrusions.

5. The assembly of claim 1, wherein the membrane is constructed polydimethylsiloxane (PDMS).

6. The assembly of claim 1, wherein the desired distance is about 100 µm to about 200 µm.

7. The assembly of claim 1, wherein gas permeable membrane has a thickness of about 50 µm to about 200 µm.

8. The assembly of claim 1, wherein the supply port of each insert is in flow communication with a supply manifold, an exhaust manifold, or both.

9. The assembly of claim 1, wherein the bottom portion of the insert includes a bottom surface, and wherein the membrane includes a plurality of upwardly extending protrusions arranged to maintain a portion of the gas permeable membrane spaced away from the bottom surface of the insert.

10. The assembly of claim 9, wherein the protrusions are spaced apart from one another in a pattern, and wherein the pattern forms a plurality of flow spaces between adjacent protrusions.

11. The assembly of claim 9, wherein the protrusions include top portions, and wherein the top portions are attached to the bottom surface of the insert.

12. The assembly of claim 1, wherein the bottom portion defines a bottom surface, and wherein the supply port and the exhaust port extend through insert to the bottom surface.

13. The assembly of claim 1, wherein the second flow channel comprises a plurality of flow channels.

* * * * *